(12) United States Patent
Hageman et al.

(10) Patent No.: US 7,351,524 B2
(45) Date of Patent: Apr. 1, 2008

(54) DIAGNOSTICS AND THERAPEUTICS FOR MACULAR DEGENERATION-RELATED DISORDERS

(75) Inventors: Gregory S. Hageman, Coralville, IA (US); Robert F. Mullins, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 559 days.

(21) Appl. No.: 10/419,305

(22) Filed: Apr. 18, 2003

(65) Prior Publication Data

US 2003/0207309 A1    Nov. 6, 2003

Related U.S. Application Data

(63) Continuation of application No. 09/845,745, filed on Apr. 30, 2001, now abandoned, which is a continuation-in-part of application No. 09/510,230, filed on Feb. 22, 2000, now abandoned.

(60) Provisional application No. 60/200,698, filed on Apr. 29, 2000.

(51) Int. Cl.
  *C12Q 1/00* (2006.01)
  *G01N 33/53* (2006.01)
(52) U.S. Cl. .............. 435/4; 435/7.1; 435/7.4; 435/7.8; 530/350; 530/380
(58) Field of Classification Search ............. 435/7.24, 435/7.4, 7.8, 18, 4, 7.1; 436/86, 821; 530/350, 530/380
See application file for complete search history.

(56) References Cited

U.S. PATENT DOCUMENTS

| | | | |
|---|---|---|---|
| 3,654,090 | A | 4/1972 | Schuurs et al. |
| 5,472,939 | A | 12/1995 | Fearon et al. |
| 5,681,571 | A | 10/1997 | Holmgren et al. |
| 5,686,598 | A | 11/1997 | North et al. |
| 5,705,380 | A | 1/1998 | North et al. |
| 5,773,573 | A | 6/1998 | Holms |
| 5,843,449 | A | 12/1998 | Boots et al. |
| 5,951,984 | A | 9/1999 | Kaneko et al. |
| 6,087,120 | A | 7/2000 | Van Oeveren et al. |
| 6,103,235 | A | 8/2000 | Neville et al. |
| 6,153,203 | A | 11/2000 | Holmgren et al. |
| 7,011,952 | B2 | 3/2006 | Hageman et al. |
| 7,108,982 | B1 | 9/2006 | Hageman |
| 2002/0015957 | A1 | 2/2002 | Hageman et al. |
| 2002/0102581 | A1 | 8/2002 | Hageman et al. |
| 2003/0017501 | A1 | 1/2003 | Hageman et al. |
| 2005/0119536 | A1 | 6/2005 | Hageman |
| 2005/0287601 | A1 | 12/2005 | Hageman et al. |
| 2006/0263819 | A1 | 11/2006 | Hageman et al. |

FOREIGN PATENT DOCUMENTS

| | | |
|---|---|---|
| WO | WO 90/15152 A1 | 12/1990 |
| WO | WO 95/17673 A | 6/1995 |
| WO | WO 97/38004 A1 | 10/1997 |
| WO | WO 00/52479 A2 | 9/2000 |
| WO | WO 01/84149 A3 | 11/2001 |

OTHER PUBLICATIONS

Roitt, I. et al. Immunology [1985 ], Roitt et al. editors. C.V. Mosby Company, St. Louis. pp. 7.1-7.14.*
Paul W. E., editor. Fundamental Immunology, 2nd edition. Raven Press, New York. [1989 ]p. 681.*
Abraha, A. and Luzio, J.; "Inhibition of the formation of the complement membrane-attack complex by a monoclonal antibody to the complement component C8a Subunit", *Biochem J*, 1989, pp. 933-936; 264, Great Britain.
Akiyama, H. et al; "Inflammation and Alzheimer's disease"; *Neurobioy of Aging 21*; May-Jun. 2000; pp. 383-421; vol. 21, No. 3.
Allikmets, R. et al; "Mutation of the Stargardt Disease Gene (ABCR) in Age-Related Macular Degeneration", *Science*, Sep. 19, 1997; pp. 1805-1807, vol. 277.
Auda, G. et al; "Measurement of complement activation products in patients with chronic rheumatic disease", *Rheumatology International*; 1990, 10(5):pp. 185-189, Springer-Verlag.
Baatrup, G. et al; "Effects of coagulation temperature on measurements of complement function in serum samples from patients with systemic lupus erythematosus", *Annuals of Rheumatic Disease*; 1992, 51(7):892-897.
Bachinsky, D. et al; "Detection of Two Forms of GP330", *American Journal of Pathology*; Aug. 1993, pp. 598-611, vol. 143, No. 2.
Bhakdi, S. & Tranum-Jensen, J.; "Membrane Damage by Complement", *Biochimica et Biophysica Acta*; 1983, pp. 343-372; 737, Elsevier Science Publishers B.V.
Bora, N.S. et al.; "Differential expression of the complement regulatory proteins in the human eye", *Investigative Ophthalmology & Visual Science*; Dec. 1993, pp. 3579-3584, vol. 34, No. 13.
Braley-Mullen; "Activation of Distinct Subsets of T Suppressor Cells with Type III Pneumococcal Polysaccharide Coupled to Syngeneic Spleen Cells", *Immunological Tolerance To Self and Non-Self*, Annals of New York Academy of Science, 1982, pp. 156-166, vol. 392.
Burger, R. et al; "The C Terminus of the Anaphylatoxin C3a Generated Upon Complement Activation Represents a Neoantigenic Determinant with Diagnostic Potential", *Journal of Immunology*, Jul. 15, 1988; pp. 553-558, vol. 141, No. 2, Printed in the U.S.A.
Buyon, J. et al.; "Assessment of Disease Activity and Impending Flare in Patients with Systemic Lupus Erythematosus", *Arthritis and Rheumatism*; Sep. 1992, pp. 1028-1037, vol. 35, No. 9.

(Continued)

*Primary Examiner*—Christina Chan
*Assistant Examiner*—F. Pierre VanderVegt
(74) *Attorney, Agent, or Firm*—Townsend and Townsend and Crew LLP

(57) ABSTRACT

The invention relates to methods for treating, preventing and diagnosing macular degeneration-related disorders.

6 Claims, 5 Drawing Sheets

OTHER PUBLICATIONS

Campbell, R. et al; "An Anion Binding Study of Vanadyl(IV) Human Serotransferrin", *Journal of Biological Chemistry*; 1977, pp. 5996-6001, vol. 252, No. 17, Printed in the U.S.A.

Caraher, E.M. et al; "Evidence for enhanced rates of complement activation in serum from patients with newly diagnosed insulin-dependent diabetes mellittus exposed to rat islet cells and complement-dependent induction of islet cell apoptosis.", *Journal of Endocrinology*; 1999, pp. 143-153, vol. 162, No. 1, Printed in Great Britain.

Chenoweth, D. et al; "Complement Activation During Cardiopulmonary Bypass", *New England Journal of Medicine*; Feb. 26, 1981; pp. 497-502, vol. 304, No. 9, Printed in the U.S.A.

Chain, B. et al; "Improvement of the in vitro T cell proliferation assay by a modified method that separates the antigen recognition and IL-2-dependent steps.". *Journal of Immunological Methods*; 1987, pp. 221-228, vol. 99.

Debrock, S. and Declerck, P.; "Characterization of common neoantigenic epitopes generated in plasminogen activator inhibitor-1 after cleavage of the reactive center loop or after complex formation with various serin proteinases.", *FEBS Letters*; 1995, pp. 243-246, vol. 376.

Delori, F. and Ben-Sira, I.; "Excitation and emission spectra of fluorescein dye in the human ocular fundus,", *Investigative Ophthalmology*; Jun. 1975, pp. 487-492, vol. 14, No. 8.

Delori, F. et al; "In Vivo Fluorescence of the Ocular Fundus Exhibits Retinal Pigment Epithelium Lipofuscin Characteristics", *Investigative Ophthalmology & Visual Science*; Mar. 1995, pp. 718-729, vol. 38, No. 3.

Detrick, B. et al.; "Class II Antigen Expression and Gamma Interferon Modulation of Monocytes and Retinal Pigment Epithelial Cells from Patients with Retinitis Pigmentosa", *Clinical Immunology and Immunopathology*, Aug. 1985, pp. 201-211, vol. 36, No. 2, San Diego, CA, U.S.A.

Edwards, A. et al; "Malattia Leventinese: Refinement of the Genetic Locus and Phenotypic Variability in Autosomal Dominant Macular Drusen", *American Journal of Ophthalmology*; Sep. 1998, pp. 417-424, vol. 126, Elsevier Science Inc.

Egerton, M. et al; "Identification of Ezrin as an 81-kDa Tyrosin-Phosphorylated Protein in T Cells", *The Journal of Immunology*, Sep. 15, 1992; pp. 1847-1852, vol. 149, No. 6, Printed in the U.S.A.

Enk, C. et al; "A Standardized Human T-lymphocyte Proliferation Assay for Detecting Soluble Accessory Factors From Monocytes", *Acta Pathol Microbiol Immunol Scand* [C], 1984, pp. 93-100, vol. 92, No. 2.

Epstein, G.A. and Rabb, M.F.; "Adult vitelliform macular degeneration: diagnosis and natural history"; *British Journal of Ophthalmology*, 1980, pp. 733-40, vol. 64.

Felbor, U. et al; "Adult vitelliform Macular Dystrophy Is Frequently Associated With Mutations in the Peripherin/RDS Gene", *Human Mutation*; 1997, pp. 301-309, vol. 10.

Felbor, U. et al; "Autosomal Recessive Sorsby Fundus Dystrophy Revisited: Molecular Evidence for Dominant Inheritance", *American Journal of Human Genetics*; 1997, pp. 57-62, vol. 60.

Fitzgibbon, J. et al; "Localisation of the human blue cone pigment gene to chromosome band 7q31.3-32", *Human Genetics*; 1994, pp. 79-80, vol. 93.

Forstrom, J.W. et al; Immunization to a syngeneic sarcoma by a monoclonal auto-anti-idiotypic antibody, *Nature*; Jun. 16, 1983; pp. 627-629, vol. 303.

Giltay, R. et al; "Sequence, Recombinant Expression and Tissue Localization of Two Novel Extracellular Matrix Proteins, *fibulin*-3 and *fibulin*-4", *Matrix Biol*, Oct. 1999, pp. 469-480, vol. 18, No. 5.

Gorski, J.; "Quantitation of Human Complement Fragment C4ai in Physiological Fluids by Competitive Inhibition Radioimmune Assay", *Journal of Immunological Methods*; 1981, pp. 61-73, vol. 47, Elsevier/North-Holland Biomedical Press.

Goslings W., et al.; "Membrane-Bound Regulators of Complement Activation in Uveal Melanomas. CD46, CD55, and CD59 in Uveal Melanomas"; *Investigative Ophthalmology & Visual Science*, Aug. 1996, pp. 1884-1891, vol. 37, No. 9.

Green, W.R.; "Histopathology of age-related macular degeneration", *Molecular Vision*, Nov. 1999, vol. 5, No. 27.

Griesinger, I.B. et al; Macular Degeneration with Highly Variable Phenotype Localized to Chromosome 6q. *American Journal of Human Genetics*; 63:A30; 1998.

Gurne, D. et al; "Antiretinal Antibodies in Serum of Patients with Age-related Macular Degeneration", *Opthalmology*; May 1991; pp. 602-607, vol. 98, No. 5.

Halliday, W.J. and Maluish, A.E.; Chapter 1: "Hemocytometer LAI: Immunological Basis and Applications", *Assessment of Immune Status by the Leukocyte Adherence Inhibition Test*; 1982; pp. 1-26, Academic Press, Inc; New York.

Hayamizu et al; "Monocyte-derived dendritic cell precursors facilitate tolerance to heart allografts after total lymphoid irradiation", *Transplantation*, 1998, pp. 1285-1291, vol. 66, No. 10.

Hintner, H. et al; "Vitronectin Shows Complement-Independent Binding to Isolated Keratin Filament Aggregates", *Journal of Investigative Dermatology*; Nov. 1989, pp. 656-661, vol. 93, No. 5.

Holz, F. et al.; "Patterns of increased in vivo fundus autofluorescence in the junctional zone of geographic atrophy of the retinal pigment epithelium associated with age-related macular degeneration.", *Graefes Arch Clin Exp Ophthalmol*; 1999, pp. 145-152, vol. 237.

Hugli, T.E. and Chenoweth, D.E.; "Biologically Active Peptides of Complement: Techniques and Significance of C3a and C5a Measurements", *Immunoassays: Clinical Laboratory Technique for the 1980s*; 1980, pp. 443-460.

Inglehearn, et al; Letter to the Editor entitled, "Loci for Autosomal Dominant Retinitis Pigmentosa and Dominant Cystoid Macular Dystrophy on Chromosome 7p Are Not Allelic", *American Journal of Human Genetics*; 1994, pp. 581-582, vol. 55.

Johnson, L.V. et al.; "A Potential Role for Immune Complex Pathogenesis in Drusen Formation"; *Exp Eye Res*, 2000; pp. 441-449, vol. 70.

Kakehashi, et al; "Differential Diagnosis of Macular Breaks By Microperimetry Using the Scanning Laser Ophthalmoscope", *Jpn J Ophthalmol*; 1996, pp. 116-122; vol. 40, No. 1.

Kaluzny; et al; "The use of indocyanine green angiography in diagnosis of occult choroidal neovascularization in age-related macular degeneration" (title translated), *Klinika Oczna*; 1999, pp. 355-359, vol. 101, No. 5, with abstract.

Kazeem, A.A. et al; "Assay of Circulating Immune Complexes by Immunonephelometry Markers of Immunonephropathy Among Young Nigerians", *East African Medical Journal*; Jun. 1990, pp. 396-403, vol. 67, No. 6.

Kelsell, R. et al; Letter to the Editor entitled, "Localization of a Gene (CORD7) for a Dominant Cone-Rod Dystrophy to Chromosome 6q", *American Journal of Human Genetics*, 1998, pp. 274-279, vol. 63.

Kiang, J. et al, "17β-Estradiol-induced Increases in Glucose-regulated Protein 78kD and 94kD Protect Human Breast Cancer T47-D Cells from Thermal Injury", *Chinese Journal of Physiology*; 1997, pp. 213-219, vol. 40, No. 4.

Kilpatrick, J. and Volanakis, J.; "Opsonic Properties of C-Reactive Protein. Stimulation by Phorbolmyristate Acetate Enables Human Neutrophils to Phagocytize C-Reactive Protein-Coated Cells", *The Journal of Immunology*, May 1985, pp. 3364-3370, vol. 134, No. 5.

Kita, T. et al; "Atherosclerosis V: The Fifth Saratoga International Conference. Oxidized-LDL and Atherosclerosis Role of LOX-1", *Annals of the New York Academy of Sciences*; 2000, pp. 95-100, vol. 902.

Klein, M. et al; "Age-Related Macular Degeneration. Clinical Features in a Large Family and Linkage to Chromosome 1q.", *Arch. Ophthalmol*; Aug. 1998, pp. 1082-1088, vol. 116.

Kohno, T. et al.; "Detection of Choroidal Neovascularization in Age-related Macular Degeneration Using Subtraction Methods in Indocyanine Green Angiography", *Bull Soc Belge Ophtalmol*; 1995, pp. 81-88, vol. 259.

Koppi, T. and Halliday, W.J.; "Further Characterization of the Cells Involved in Leukocyte Adherence Inhibition with Murine Tumor Extracts", *Cellular Immunology*; 1982; pp. 394-406, vol. 66.

Kovacs, H. et al; "Evidence That C1q Binds Specifically to $C_h2$-like Immuinoglobulin γ Motifs Present in the Autoantigen Calreticulin and Interferes with Complement Activation", *Biochemistry*; 1998, pp. 17865-17874, vol. 37, No. 51.

Krapf, F. et al; "Determination of Complement Activating Circulating Immune Complexes and an Example for Antigen Specific Immune Complex Assays", *Journal of Clinical Lab Immunology*; 1986, pp. 183-187, vol. 21.

Kuck, H. et al.; Diagnosis of Occult Subretinal Neovasculariztion in Age-related Macular Degeneration by Infrared Scanning Laser Videoangiography, *Retina*: 1993, pp. 36-29, vol. 13, No. 1.

Kylstra, J.A. et al; Letter to the Journal entitled, "Cone-rod retinal dystrophy in a patient with neurofibromatosis type 1", *Canadian Journal of Ophthalmology*; 1993, pp. 79-80, vol. 28, No. 2.

Langlois, P. et al; "Plasma concentrations of complement-activation complexes correlate with disease activity in patients diagnosed with isolated central nervous system vasculitis", *Journal of Allergy Clinical Immunology*; Jan. 1989, pp. 11-16, vol. 83, No. 1.

Lawn et al; "The Sequence of Human Serum Albumin cDNA and Its Expression in *E. coli*", *Nucleic Acids Research*, 1981, pp. 6103-6114, vol. 9, No. 22.

Li, X. et al.; "A pineal reluatory element (PIRE) mediates transactivation by the pineal/retina-specific transcription factor CRX", *Proc. Natl. Acad. Sci. USA*; 1998, pp. 1876-1881, vol. 95.

Linder, E. et al; "An Immunofluorescence Assay for Complement Activation by the Classical Pathway", *Journal of Immunological Methods*; 1981, pp. 49-59, vol. 47.

Lotery, A.J. et al; "Localisation of a Gene for Central Areolar Choroidal Dystrophy to Chromosome 17p", *Investigative Ophthalmology & Visual Science*; Feb. 15, 1996; pp. 1124, vol. 37, No. 3. (Abstract only).

Lubinski, W. et al; "Foveal electroretinogram-application in diagnosis of macular diseases. Preliminary report.", *Klin Oczna*; 1998, pp. 263-268, vol. 100, No. 5. (Translated abstract of document included).

Lynch, N. et al; "Characterisation of the rat and mouse homologues of gC1qBP, a 33 kDa glycoprotein that binds to the globular 'heads' of C1q", *FEBS Letters*; 1997, pp. 111-114, vol. 418.

Mahant, S., et al.; "Retinal dystrophy in 18q- (de Grouchy) syndrome.", *Am. J. Hum. Genet.*; 1995, p. A96, vol. 57, (Abstract only).

Marmorstein, Alan D., et al; "Bestrophin, the product of the Best vitelliform macular dystrophy gene (*VMD2*), localizes to the basolateral plasma membrane of the retinal pigment epithelium"; *PNAS*; Nov. 7, 2000; pp. 12758-12763; vol. 97, No. 23.

Marquardt, A. et al; "Mutations in a novel gene, *VMD2*, encoding a protein of unknown properties cause juvenile-onset vitelliform macular dystrophy (Best's disease)", *Human Molecular Genetics*; 1998, pp. 1517-1525, vol. 7, No. 9, Oxford University Press.

Marx; "Testing of Autoimmune Therapy Begins", *Science*, Apr. 1991, pp. 27-28, vol. 252.

Metzler and Wraith; "Inhibition of experimental autoimmune encephalomyelitis by inhalation but not oral administration of the encephalitogenic peptide: influence of MHC binding affinity", *International Immunology*, 1993, pp. 1159-1165, vol. 5, No. 9.

Milis, L. et al; "Vitronectin-mediated inhibition of complement: evidence for different binding sites for C5b-7 and C9", *Clin Exp Immunol.*; 1993, pp. 114-119, vol. 92.

Minh, Do-Quang et al; "Serial complement measurements in patients with leukaemia", *Clin Lab Haematol.*; 1983, pp. 23-34, vol. 6.

Mold, C. et al; "CR2 is a Complement Activator and the Covalent Binding Site for C3 During Alternative Pathway Activation by Raji Cells", *Journal of Immunology*; Mar. 15, 1988; pp. 1923-1929, vol. 140, No. 6.

Mousa, S. et al. "Role of Hypoxia and Extracellular Matrix-Integrin Binding in the Modulation of Angiogenic Growth Factors Secretion by Retinal Pigmented Epithelial Cells", *Journal of Cellular Biochemistry*, 1999, pp. 135-143, vol. 74.

Mullins, R. et al.; "Drusen associated with aging and age-related macular degeneration contain proteins common to extracellular deposits associated with atherosclerosis, elastosis, amyloidosis, and dense deposit disease", *The FASEB Journal*; May 2000, pp. 835-846, vol. 14.

Munroe, P. et al; "Spectrum of Mutations in the Batten Disease Gene, CLN3", *American Journal of Human Genetics*; 1997, pp. 310-316, vol. 61.

Newell, S., et al.; :Hemolytic and antigentic measurements of complement. A comparison of serum and plasma samples in normal individuals and patients; *J Lab Clin Med*; Sep. 1982; pp. 437-444; vol. 100, No. 3.

Ng, Y.C. et al.; "Immune complexes and erythrocyte CR1 (complement receptor type 1): effect of CR1 numbers on binding and release reactions", *Clin Exp Immunol.*; 1988, pp. 481-485, vol. 71.

Padma, T. and Murty, J.S., "Association of Genetic Markers with Some Eye Diseases", *Acta Anthropogenetica*, 1983, pp. 1-12, vol. 7, No. 1.

Payne, A. et al; "A mutation in guanylate cyclase activator 1A (GUCA1A) in an autosomal dominant cone dystrophy pedigree mapping to a new locus on chromosome 6p21.1", *Human Molecular Genetics*; 1998, pp. 273-277, vol. 7, No. 2, Oxford University Press.

Penfold, P. et al; "Autoantibodies to retinal astrocytes associated with age-related macular degeneration", *Graefe's Archive for Clinical and Experimental Ophthalmology*, 1990, pp. 270-274, vol. 228.

Pintér, C. et al; "Presence of autoantibodies against complement regulatory proteins in relapsing-remitting multiple sclerosis", *Journal of Neurovirology*; 2000, pp. S42-S46, vol. 6, Suppl. 2, Macmillan Publishers Ltd.

Quax-Jeuken, Y. et al; "βs-Crystallin: structure and evolution of a distinct member of the βγ-superfamily", *EMBO Journal*; 1985, pp. 2597-2602, vol. 4, No. 10.

Rabb, M. et al, "A North Carolina Macular Dystrophy Phenotype in a Belizean Family Maps to the MCDR1 Locus", *American Journal of Ophthalmology*, Apr. 1998, pp. 502-508, vol. 125, No. 4.

Ratnoff, W. et al.; "Immunohistochemical Localization of C9 Neoantigen and the Terminal Complement Inhibitory Protein CD59 in Human Endometrium", *American Journal of Reproductive Immunology*; 1995, pp. 72-79, vol. 34, Munksgaard, Copenhagen.

Ravelli, A. et al; "IgG autoantibodies to complement C1q in pediatric-onset systemic lupus erythematosus", *Clinical and Experimental Rheumatology*; 1997, pp. 215-219, vol. 15.

Reaven, Peter; "Mechanisms of Atherosclerosis: Role of LDL Oxidation", *Free Radicals in Diagnostic Medicine*, 1994, pp. 113-128, Plenum Press, New York, U.S.A.

Rodrick, M. et al; "An Evaluation of Two Antigen Nonspecific Assays for Circulating Immune Complexes Using an Model System", *J. Clin Lab Immunol*; 1982, pp. 193-198, vol. 7, No. 3.

Sacks, J.G. et al; "The Pathogenesis of Optic Nerve Drusen", *Archives of Ophthalmology*, Mar. 1997, pp. 425-428, vol. 95, No. 3.

Seymour, A. et al; "Linkage Analysis of X-linked Cone-Rod Dystrophy: Localization to Xp11.4 and Definition of a Locus Distinct from RP2 and RP3", *Am. J. Hum. Genet.*; 1998, pp. 122-129, vol. 62.

Slingsby, C. and Bateman, O.A.; "Rapid Separation of Bovine β-Crystallin Subunits βB1, βB2, βB3, βA3 and βA4", *Exp Eye Res*; 1990, pp. 21-26, vol. 51.

Small, K. et al.; "Mapping of Autosomal Dominant Cone Degeneration to Chromosome 17p", *American Journal of Ophthalmology*; 1996, pp. 13-18, vol. 121, No. 1.

Spraul, et al; "Optical Coherence Tomography of Age-Related Macular Degeneration. Correlation of Diagnostic Techniques of Fluorescence angiography and OCT" (title translated) *Klin Monatsbl Augenheilkd*; Mar. 1998, pp. 141-148, vol. 212.

Stone, Edwin M., et al.; "A single *EFEMP1*mutation associated with both Malattia Leventinese and Doyne honeycomb retinal dystrophy"; *Nature Genetics*; Jun. 1999; pp. 199-202; vol. 22.

Strife, C. et al; "Autoantibody to complement neoantigens in membranoproliferative glomerulonephritis", *The Journal of Pediatrics*; May 1990, pp. S98-S102, vol. 116, No. 5.

Suzuki et al.; "Complete amino acid sequence of human vitronectin deduced from cDNA. Similarity of cell attachment sites in vitronectin and fibronectin", *EMBO J*, 1985, pp. 2519-2524, vol. 4, No. 10.

Tanaka, S. et al; "Assay of classical and alternatie pathway activities of murine complement using antibody-sensitized rabbit erythrocytes", *Journal of Immunological Methods*; 1986, pp. 161-170, vol. 86, Elsevier Science Publishers B.V.

Thomson et al; "Microchimerism, Dendritic Cell Progenitors and Transplantation Tolerance", *Stem Cells*; 1995, pp. 622-639, vol. 13.

Tomimori-Yamashita, J. et al; "Antibody-based enzyme-linked immunosorbent assay for determination of anti-PGL-I specific circulating immune complex in leprosy patients.", *Lepr Rev*; 1999, pp. 261-271, vol. 70.

Tran, H. et al.; "Human Fibulin-1D: Molecular Cloning, Expression and Similarity with S1-5 Protein, a New Member of the Fibulin Gene Family", *Matrix Biology*, 1997, pp. 479-493, vol. 15.

Trentham et al; "Effects of Oral Administration of Type II Collagen on Rheumatoid Arthritis", *Science*; 1993, pp. 1727-1730, vol. 261.

Tschopp, J. et al.; "Clusterin, the Human Apolipoprotein and Complement Inhibitor, Binds to Coplement C7, C8β, and the b Domain of C9", *Journal of Immunology*.; Aug. 15, 1993; pp. 2159-2165, vol. 151, No. 4, Printed in the U.S.A.

Van Dijk, H. et al.; "Determination of Alternative Pathway of Complement Activity in Mouse Serum Using Rabbit Erythrocytes", *Journal of Immunolical Methods*; 1890, pp. 29-39, vol. 36, Elsevier/North-Holland Biomedical Press.

Volanakis, J.; C-Reactive Protein and the Plasma Protein Response to Tissue Injury. Part IV. Biological Properties and Function of CRP and SAP: "Complement Activation by C-Reactive Protein Complexes", *Annals of the New York Academy of Sciences*; 1982, pp. 235-250, vol. 389.

Warburg, M., et al; "Deletion Mapping of a Retinal Cone-Rod Dystrophy: Assignment to 18q211", *American Journal of Medical Genetics*; 1991, pp. 288-293, vol. 39.

Wexler et al; "Primary amino acid sequence and structure of human pyruvate carboxylase", *Biochimica et Biophysica Acta*, 1994, pp. 46-52, vol. 1227.

Yamanaka, R. et al; "CCAAT/enhancer binding protein ∈ is preferentially up-regulated during granulocytic differentiation and its functional versatility is determined by alternative use of promoters and differential splicing.", *Proc Natl Acad Sci USA*; Jun. 1997, pp. 6462-6467, vol. 94.

Yuzawa, M. et al; "Clinical evaluation of indocyanine green videoangiography in the diagnosis of choroidal neovascular membrane associated with age-related macular degeneration", *European Journal of Ophthalmology*; 1992, pp. 115-121, vol. 2, No. 3.

Zhang, K. et al; "A dominant Stargardt 's Macular Dystrophy Locus Maps to Chromosome 13q34", *Arch. Ophthalmol*.; Jun. 1994, pp. 759-764, vol. 112.

Zhang, Y, et al; "Lysis via the lectin pathway of complement activation: minireview and lectin pathway enhancement of endotoxin-initiated hemolysis"; *Immunopharmacology*; May 1999; pp. 81-90; vol. 42.

Bird, A. "Age-related macular disease," Br. J. Ophthalmol., 80, 2-3, 1996.

Bird, A. "Bruch's membrane change with age," Br. J. Ophthalmol., 763, 166-168, 1992.

Bressler, N., et al. "Clinicopathologic correlation of drusen and retinal pigment epithelial abnormalities in age-related macular degeneration," Retina, 14, 130-142, 1994.

Bressler, S., et al. "Relationship of drusen and abnormalities of the retinal pigment epithelium to the prognosis of neovascular macular degeneration," Arch. of Ophthalmol., 108, 1442-1447, 1990.

Burns, R., and Feeney-Burns, L., Transactions of the American Ophthalmologic Society, 78, 206-225, 1980.

Chen, H. et al. "An immunologic study of age-related macular degeneration" Yan Ke Xue Bao, Sep. 1993, pp. 113-120, vol. 9, No. 3.

De La Paz, M., et al. "Analysis of the stargardt disease gene (ABCR) in age-relate macular degeneration," Invest. Ophthalmol. Vis. Sci. (Suppl), 39, S915, 1980.

Duvall, J., and Tso, M. "Cellular mechanisms of resolution of drusen after laser coagulation," Arch. Ophthalmol., 103, 694-703, 1985.

Duvall-Young, J., et al. "Fundus changes in (type II) mesangiocapillary glomerulonephritis simulating drusen: a histopathological report," Br. J. Ophthalmol., 73, 297-302, 1989.

Eagle, R. "Mechanisms of maculopathy," Ophthalmol., 91, 613-25, 1984.

Eisner, A., et al. "Sensitivities in older eyes with good acuity: eyes whose fellow eye has exudative AMD," Invest. Ophthalmol. Vis. Sci., 28, 1832-1837, 1987.

Elman, M., and Fine, S. "Exudative age-related macular degeneration," in S. Ryan (Ed.), The Retina (pp. 175-200). St Louis: CV Mosby, 1992.

Esser et al. "The significance of vitronectin in proliferative diabetic retinopathy," Graefes Archive for Clinical and Experimental Ophthalmology, 232 (8) 477-81, 1994.

Farkas, T., et al. "The histochemistry of drusen," Amer. J. Ophthalmol., 71, 1206-1215, 1971.

Farkas, T., et al. The ultrastructure of drusen, Amer. J. Ophthalmol., 71, 1196-1205, 1971.

Feeney-Burns, et al. "Lysosomal enzyme cytochemistry of human RPE, bruch's membrane and drusen," Invest. Ophthalmol. Vis. Sci., 28, 1138-1147, 1987.

Feeney-Burns, L. et al. "The fate of immunoreactive opsin following phagocytosis by pigment epithelium in human and monkey retinas," Invest. Ophthalmol. Vis. Sci., 29, 708-719, 1988.

Feeney-Burns, L., and Ellersieck, M. "Age-related changes in the ultrastructure of bruch's membrane," Amer. J. Ophthalmol., 100, 686-697, 1985.

Frenneson, I., and Nilsson, S. "Laser photocoagulation of soft drusen in early age-related maculopathy (ARM). The one-year results of a prospective, randomised trial," Eur. J. Ophthalmol., 6, 307-314, 1996.

Frennesson, C., et al. "Colour contrast sensitivity in patientswith soft drusen, an early stage of ARM,", Documenta Ophthalmologica, 90, 377-86, 1995.

Grossiklaus, et al. "Immunohistochemical and histochemical properties of surgically excised subretinal neovascular membranes in age-related macular degeneration,"American Journal of Ophthalmology 114 (4), 464-72, 1992.

Hageman, et al. "Vitronectin is a constituent of ocular drusen and the vitroectin gene is expressed in human retinal pigmented epithelial cells," FASEB Journal, 13(3), 477-84, 1999.

Heidenkummer, et al. "Surgical extraction of subretinal pseudotumors in age related macular degeneration," Ophthalmologe, 92 (5), 631-639, 1995.

Holz, F., et al. "Analysis of lipid deposits extracted from human macular and peripheral bruch's membrane," Arch. Ophthalmol., 112, 402-406, 1994.

Ishibashi, T., et al. "Formation of drusen in the human eye," Amer. J. Ophthalmol., 101, 342-353, 1986.

Ishibashi, T., et al. "Pathogenesis of drusen in the primate," Invest. Ophthalmol. Vis. Sci., 27, 184-193, 1986.

Keltner, JL & Thirkill, CE "The 22-kDa antigen in optic nerve and retinal diseases" *J. Neuroopthamol.*, Jun. 1999, pp. 71-83, vol. 19, No. 2.

Killingsworth, M., et al. "Macrophages related to bruch's membrane in age-related macular degeneration," Eye, 4, 613-621, 1990.

Klaver et al., "Genetic association of apolipoprotein E with age-related macular degeneration," Am J. of Human Genetics, 63 (1), 200-6, 1998.

Lewis, H., et al. "Chorioretinal Juncture, multiple extramacular drusen," Ophthalmol., 93, 1098-1112, 1986.

Loeffler, K., and Mangini, M. "Immunolocalization of ubiquitin and related enzymes in humna retina and retinal pigment epithelium," Graefe's Arch. Clin. Exp. Ophthalmol., 235, 248-54, 1997.

Loeffler, K., et al. "Immunoreactivity against tau, amyloid precursor protein; and beta-amyloid in the human retina," Invest. Ophthalmol. Vis. Sci., 36, 24-31, 1995.

Midena, E., et al. "Macular function impairment in eyes with early age-related macular degeneration," Invest. Ophthalmol. Vis. Sci., 38, 469-477, 1997.

Newsome, D., et al. "Detection of specific extracellular matrix molecules in drusen, bruch's membrane and cillary body," Amer. J. Ophthalmol., 104, 373-381, 1987.

Newsome, D., et al. "Macular degeneration and elevated serum ceruloplasmin," Invest. Ophthalmol. Vis. Sci., 27, 1675-80, 1986.

Pauleikhoff, D., et al. "Drusen as risk factors in age-related macular disease," Amer. J. Ophthalmol., 109, 38-43, 1990.

Pauleikhoff, D., et al. "Correlation between biochemical composition and fluorescein binding of deposits in bruch's membrane," Ophthalmol., 99, 1548-1553, 1992.

Penfold, P. et al. "Modulation of major histocompatibility complex II expression in retinas with age-related macular degeneration," Invest. Ophthalmol. Vis. Sci., 38, 2125-33, 1997.

Penfold, P. et al. "Senile macular degeneration," Invest. Ophthalmol. Vis. Sci., 27, 364-71, 1986.

Penfold, P. et al. "Senile macular degeneration: the involvement of immunocompetent cells," Graefe's Arch. Clin. Exp. Ophthalmol., 223, 69-76, 1985.

Sarks, J., et al. "Evolution of soft drusen in age-related macular degeneration" (1994), Eye, 8, 269-283.

Sarks, S. "Aging and degeneration in the macular region: a clinicopathological study," Br. J. Ophthalmol., 60, 324-341, 1976.

Sarks, S. "Drusen and their relationship to senile macular degeneration," Aust. J. Ophthalmol., 8, 117-30, 1980.

Sarks, S. "Drusen patterns predisposing to geographic atrophy of the retinal pigment epithelium," Austr. J. Ophthalmol., 10, 91-97, 1982.

Sarks, S., and Sarks, J. "Age-related macular degeneratio: atrophic form," in S. Ryan (Ed.), The Retina St. Louis: CV Mosby, 1989.

Sarks, S., et al., Patterns in macular degeneration. In S. Ryan, A. Dawson, and H. Little (Eds.), Retinal Diseases (pp. 87-93). Orlando: Grune and Stratton, 1985.

Sarks, S., et al. "Softening of drusen and subretinal neovascularization," Trans. Ophthalmol. Soc. U.K., 100, 414-422, 1980.

Sokal, I. et al. "GCAP1(Y99C) mutant is constitutively active in autosomal dominant cone dystrophy," Mol. Cell. 2:129-133, 1998.

Souied, et al. "The epilon4 allele of the apolipoprotein E gene as a potential protective factor for exudative age-related macular degeneration," Am. J. of Ophthalmology, 125 (3) 353-9, 1998.

Spraul, C., and Grossniklaus, H. "Characteristics of drusen and bruch's membrane in postmortem eyes with age-related macular degeneration," Arch. Ophthalmol., 115, 267-73, 1997.

Tso, Mo "Experiments on visual cells by nature and man: in search of treatment for photoreceptor degeneration. Friedenwald lecture." *Invest Ophthalmol Vis Sci*, Dec. 1989, pp. 2430-2454, vol. 30, No. 12.

van der Schaft, T., et al. "Early stages of age-related macular degeneration: an immunofluorescence and electron microscopy study," Br. J. Ophthalmol., 77, 657-661, 1993.

Vinding, T. "Occurrence of drusen, pigmentary changes and exudative changes in the macula with reference to age-related macular degeneration," Acta Opthalmologica, 68, 410-414, 1990.

Young, R. "Pathophysiology of age-related macular degeneration" Surv. Ophthalmol., 31, 291-306, 1987.

Johnson et al., "Complement Activation and Inflammatory Processes in Drusen Formation and Age Related Macular Degeneration," *Exp. Eye Res.*, 73:887-896 (2001).

Hageman et al., "An Integrated hypothesis That Considers Drusen as Bioomarkers of Immune-Mediated Processes at the RPE-Bruch's Membrane Interface in Aging and Age-Related macular Degeneration," *Progress in Retinal and Eye Research*, 20(6):705-732 (2001).

Hageman et al., "Molecular composition of drusen as related to substructural phenotype," *Molecular Vision*, vol. 5, 10 pages (1999).

Mullins et al., "Histochemical Comparison of Ocular "Drusen" in Monkey and Human," pp. 1-10 from *Degenerative Retinal Diseases*, Plenum Press, New York (1997).

Office Action mailed Jan. 26, 2007and amendment mailed Nov. 21, 2006 in Pending U.S. Appl. No. 09/949,261 (Hageman et al.).

Office Action mailed Feb. 28, 2007 and amendment filed Nov. 13, 2006 in Pending U.S. Appl. No. 11/021,465 (Hageman et al.).

Office Action mailed Jan. 24, 2007 and amendment filed Jul. 23, 2007 in Pending U.S. Appl. No. 11/205,370 (Hageman et al.).

* cited by examiner

DIAGNOSTICS AND THERAPEUTICS FOR MACULAR DEGENERATION-RELATED DISORDERS

CROSS-REFERENCE TO RELATED APPLICATIONS

This application is a continuation of U.S. patent application Ser. No. 09/845,745, filed Apr. 30, 2001 now abandoned, which is a continuation-in-part of U.S. patent application Ser. No. 09/510,230, filed Feb. 22, 2000 now abandoned, and which claims the benefit of U.S. Provisional Application No. 60/200,698, filed Apr. 29, 2000. The full disclosures of these applications are incorporated herein by reference for all purposes.

FIELD OF THE INVENTION

The invention relates in general to therapeutics and diagnostics for macular degeneration-related disorders or diseases. The invention finds application in the biomedical sciences.

BACKGROUND OF THE INVENTION

Macular degeneration is a clinical term that is used to describe a variety of diseases that are all characterized by a progressive loss of central vision associated with abnormalities of Bruch's membrane, the neural retina and the retinal pigment epithelium. These disorders include very common conditions that affect older subjects (age-related macular degeneration or AMD) as well as rarer, earlier-onset dystrophies that in some cases can be detected in the first decade of life. Other maculopathies include North Carolina macular dystrophy (Small, et al., 1993), Sorsby's fundus dystrophy (Capon, et al., 1989), Stargardt's disease (Parodi, 1994), pattern dystrophy (Marmor and Byers, 1977), Best disease (Stone, et al., 1992), dominant drusen (Deutman and Jansen, 1970), and radial drusen ("malattia leventinese") (Heon, et al., 1996).

Histopathologic studies have documented significant and widespread abnormalities in the extracellular matrices associated with the RPE, choroid, and photoreceptors of aged individuals and of those with clinically-diagnosed AMD (Sarks, 1976; Sarks, et al., 1988; Bird, 1992a; van der Schaft, et al., 1992; Green and Enger, 1993; Feeney-Burns and Ellersieck, 1985; Young, 1987; Kincaid, 1992). The most prominent extracellular matrix (ECM) abnormality is drusen, deposits that accumulate between the RPE basal lamina and the inner collagenous layer of Bruch's membrane (FIG. 1).

A number of studies have demonstrated that the presence of macular drusen is a strong risk factor for the development of both atrophic and neovascular AMD (Bressler, et al., 1994; Bressler, et al., 1990; Macular Photocoagulation Study). Drusen causes a lateral stretching of the RPE monolayer and physical displacement of the RPE from its immediate vascular supply, the choriocapillaris. This displacement creates a physical barrier that may impede normal metabolite and waste diffusion between the choriocapillaris and the retina. It is likely that wastes may be concentrated near the RPE and that the diffusion of oxygen, glucose, and other nutritive or regulatory serum-associated molecules required to maintain the health of the retina and RPE are inhibited. It has also been suggested that drusen perturb photoreceptor cell function by placing pressure on rods and cones (Rones, 1937) and/or by distorting photoreceptor cell alignment (Kincaid, 1992).

The complement system consists of a group of globulins in the serum of humans (Hood, L. E. et al. 1984, Immunology, 2d Edition, The Benjamin/Cummings Publishing Co., Menlo Park, Calif., p. 339; See also, U.S. Pat. Nos. 6,087, 120 and 5,808,109). Complement activation plays an important role in the mediation of immune and allergic reactions (Rapp, H. J. and Borsos, T., 1970, Molecular Basis of Complement Action, Appleton-Century-Crofts (Meredith), N.Y.). The activation of complement components leads to the generation of a group of factors, including chemotactic peptides that mediate the inflammation associated with complement-dependent diseases. The activities mediated by activated complement proteins include lysis of target cells, chemotaxis, opsonization, stimulation of vascular and other smooth muscle cells, degranulation of mast cells, increased permeability of small blood vessels, directed migration of leukocytes, and activation of B lymphocytes, macrophages and neutrophils (Eisen, H. N., 1974, Immunology, Harper & Row, Publishers, Inc., Hagerstown, Md., p. 512).

There are three major pathways of complement activation. First, the "classical pathway," which is activated by antibody/antigen binding. Second, the "lectin pathway" or "collecting pathway," is activated by the binding of acute phase reactant mannose-binding protein (MBP; or mannose-binding lectin, MBL) to a complex carbohydrate. Third, the "alternative pathway," which involves the recognition of certain polysaccharides (e.g., on microbial surface) and is activated by the presence of a specific substrate called C3bB, a complex of complement proteins. See, e.g., Cooper, Adv Immunol, 37(-HD-):151-216, 1985; Fearon & Austen, J. Exp. Med. 146: 22-33, 1977; Pangburn et al., 266: 16847-53, 1991; Matsushita et al., Microbiol Immunol, 40(12):887-93, 1996; and Turner et al., Res Immunol, 147(2):110-5, 1996. The major classical pathway components are designated C1q, C1r, C1s, C4, C2, C3, C5, C6, C7, C8, C9. The main alternative pathway components are designated Factor B, Factor D, Properdin, H and I. In addition to MBL, the lectin pathway components also include MASP-1 and MASP-2 (Thiel et al., Nature, 386:506-10, 1997). It is also known that more than one pathway can be involved in a single disease process, as in Alzheimer's disease (Akiyama et al., Neurobiol Aging, 21:383-421 2000).

Initiation of the classical pathway begins with antibody binding to a specific antigen. C1q binds the altered Fc region of IgG or IgM that has bound antigen. Upon binding, C1r activates C1s which initiates the activation unit by cleaving a peptide from both C4 and C2. C1s thus cleaves C4 into C4a and C4b and C2 into C2a and C2b. C2a binds to C4b forming C4b2a. C4b2a, the C3 convertase, is a proteolytic enzyme. It cleaves C3 into C3b, which may bind to the activating surface, and C3a which is released into the fluid phase. C3 convertase has the ability to cleave many C3 molecules. This could result in the deposition of a large number of C3b molecules on the activating surface. However, due to the labile nature of C3b, very few molecules actually bind. C4b2a3b, the C5 convertase, is formed when C3 is cleaved. C5 convertase, also an enzyme, can cleave many C5 molecules into C5a and C5b.

The alternative pathway provides natural, non-immune defense against microbial infections. In addition, this pathway amplifies antibody-antigen reactions. Alternative pathway recognition occurs in the presence of C3b and an activating substance such as bacterial lipoprotein, surfaces of certain parasites, yeasts, viruses and other foreign body surfaces, such as biomaterials. C3b originates from classical pathway activation and/or from natural spontaneous hydrolysis of C3. The resulting C3b binds to the surface of the activating substance. In the presence of magnesium, Factor B binds to the C3b which is bound to the activating surface. Factor D then cleaves B, releasing the Ba fragment and forming C3bBb. Properdin stabilizes the C3bBb complex and protects it from decay. C3bBbP is the alternative pathway convertase. It also has the ability to cleave many C3 molecules. Cleavage of C3 results in the formation of C3bBb3b, the C5 convertase. This enzyme is also stabilized by P to form C3bBb3bP. C5 convertase can cleave many molecules of C5 into C5a and C5b.

Binding of MBL to carbohydrates triggers the lectin pathway. MBL is structurally related to the complement C1, C1q, and seems to activate the complement system through an associated serine protease known as MASP-1 or p100, which is similar to C1r and C1s of the classical pathway. MBL binds to specific carbohydrate structures found on the surface of a range of microorganisms, including bacteria, yeasts, parasitic protozoa and viruses, and exhibits antibacterial activity through killing mediated by the terminal, lytic complement components or by promoting phagocytosis. The level of MBL in plasma is genetically determined, and deficiency is associated with frequent infections in childhood, and possibly also in adults. In addition, a further MBL-associated serine protease (MASP-2) was identified which shows a striking homology with the previously reported MASP (MASP-1) and the two C1q-associated serine proteases C1r and C1s (see, e.g., Thiel et al., Nature, 386:506-10, 1997).

The membrane attack complex C5b-9 (also termed complement terminal complex, MAC, or SC5b-9) is common to the complement pathways (see, e.g., Morgan, Crit Rev Immunol, 19(3):173-98, 1999). It begins with the cleavage of C5 by C5 convertase generated during either classical or alternative pathway activation. When C5 is cleaved, C5a is released into the fluid phase while C5b attaches to the activating surface at a binding site distinct from that of C3b. One molecule each of C6 and C7 binds to C5b to form a stable trimolecular complex to which C8 binds. Then, up to 6 molecules of C9 can bind to C8 enhancing the effectiveness of the attack complex to induce membrane damage if the activating surface is a microorganism.

The significance of complement activation is not limited to membrane damage resulting from the attack complex. The active peptides released in the course of complement activation contribute to the immune response by increasing vascular permeability and contraction of smooth muscle, promoting immune adherence, granulocyte and platelet aggregation, enhancing phagocytosis, and directing the migration of neutrophils (PMN) and macrophages to the site of inflammation.

The cleavage of C3 and C5 results in the release of two small biologically active peptides, C3a and C5a. The peptides act as anaphylatoxins. They amplify the immune response by causing the release of histamine, slow releasing substance of anaphylaxis (SRS-A), and heparin from basophils and mast cells. These substances increase capillary permeability and contraction of smooth muscle resulting in edema and inflammation.

In addition to its role as an anaphylatoxin, C5a is a potent chemotactic factor. This mediator causes the directed migration of leukocytes including dendritic cells and monocytes to the site of inflammation so these leukocytes will phagocytize and clear immune complexes, bacteria and viruses from the system.

In a process known as immune adherence, C3b or C4b deposited on a soluble immune complex or surface permit binding of complement receptors on PMN, macrophages, red blood cells and platelets. In these cases C3b and C5b are considered opsonins as their presence results in more effective phagocytosis.

New diagnostics and therapeutics for macular degeneration-related disorders are needed. For example, there is currently no reliable biochemical or genetic means in routine use for diagnosing, e.g., AMD. In addition, there is no therapy currently in use that significantly slows the degenerative progression of AMD for the majority of subjects. Current AMD treatment is limited to laser photocoagulation of the subretinal neovascular membranes that occur in 10-15% of affected subjects. The latter may halt the progression of the disease but does not reverse the dysfunction, repair the damage, or improve vision.

SUMMARY OF THE INVENTION

The present inventions provides methods for diagnosing, or identifying a predisposition to the development of, a macular degeneration-related disorder in a subject by detecting in a biological sample from the subject an abnormal activity or an abnormal level of at least one complement pathway associated molecule, or an abnormal cellular activity mediated by the complement pathway. In some methods, the subject is free of complement related diseases other than macular degeneration-related disorders. In some methods, the detecting step also includes detecting at least one macular degeneration-associated genetic marker, drusen-associated phenotypic marker, or drusen-associated genotypic marker in the subject. In some methods, the detecting step further examines the subject with an ophthalmologic procedure. In some methods, the further examining step detects damages to the choriocapillaris of said subject.

Macular degeneration-related disorders that can be diagnosed with methods of the present invention include age-related macular disorder (AMD), North Carolina macular dystrophy, Sorsby's fundus dystrophy, Stargardt's disease, pattern dystrophy, Best disease, dominant drusen, and malattia leventinese. Other diseases or disorders include retinal detachment, chorioretinal degenerations, retinal degenerations, photoreceptor degenerations, RPE degenerations, mucopolysaccharidoses, rod-cone dystrophies, cone-rod dystrophies, and cone degenerations.

Samples from the subject that can be used for the diagnostics of the present invention include eye fluid, urine, blood plasma, serum, or whole blood. In some methods, the diagnosis is directed to a serum autoantibody. In some methods, the autoantibody specifically binds to a complement pathway associated molecule, a RPE protein, a choroid protein (include proteins of the Bruch's membrane), a retina protein, circulating molecules or autoantigens that bind to these ocular tissues, or a neoantigen. In some methods, the abnormal activity to be detected is an abnormal level of a complement-pathway molecules. In some methods, the abnormal level to be detected is the level of complement pathway associated molecule such as haptoglobin, Ig kappa chain, Ig lambda chain, or Ig gamma chain. In other methods, the abnormal level to be detected is the expression level of clusterin, C6 or C5b-9 complex.

In some methods of the present invention, the abnormal activity of complement system to be detected is a variant form of a nucleic acid encoding a complement pathway associated protein. The nucleic acid can be a mRNA, cDNA, or genomic DNA. The variant nucleic acid can have a point mutation, a frameshift mutation, or a deletion relative to the wild type nucleic acid. In some methods, the variant nucleic acid is detected by measuring levels of complement pathway associated molecule or complement activities in urine, blood plasma, serum, whole blood sample, or eye fluid from the subject. In some methods, the complement activities are detected by a hemolysis assay, T cell proliferative assay, or an immunological assay.

The present invention also provides methods for treating or preventing the development of a macular degeneration in a subject suffering from or at risk of developing a macular degeneration-related disorder. The methods comprise administering to the subject an effective amount of a therapeutic agent which modulates an activity or level of at least one complement pathway associated molecule, or a cellular activity mediated by the complement pathway. In some methods, the subject has a macular degeneration-related disorder. In other methods, the subject is at risk of developing a macular degeneration-related disorder. In some methods, the subject is free of complement-related diseases other than macular degeneration-related disorders.

The diseases or disorders that can be treated with the methods of the present invention include age-related macular disorder, North Carolina macular dystrophy, Sorsby's fundus dystrophy, Stargardt's disease, pattern dystrophy, Best disease, dominant drusen, and malattia leventinese. They also include retinal detachment, chorioretinal degenerations, retinal degenerations, photoreceptor degenerations, RPE degenerations, mucopolysaccharidoses, rod-cone dystrophies, cone-rod dystrophies, and cone degenerations.

In some methods, the therapeutic agent modulates level of a complement pathway associated molecule. In some methods, the complement pathway associated molecule whose level is to be modulated is anaphylatoxin C3a, anaphylatoxin C5a, C6, clusterin, haptoglobin, Ig kappa chain, Ig lambda chain, or Ig gamma chain. In some methods, the agent modulates protein level of said complement pathway associated molecule. Some methods further comprise detecting the level with urine, blood plasma, serum, whole blood, or eye fluid from the subject.

In some methods of the present invention, the therapeutic agents modulates an enzymatic activity of a complement protein or a complement pathway associated molecule. In some methods, the enzymatic activity to be modulated is catalysis of conversion of C3 into C3a and C3b, conversion of C5 into C5a and C5b, or cleavage of Factor B into Ba and Bb. Some methods further comprise detecting the enzymatic activity by a hemolytic assay or an immunological assay. In some methods, the enzymatic activity is detected with urine, blood plasma, serum, whole blood, or eye fluid from the subject.

In some methods of the present invention, the therapeutic agents modulates a cellular activity responsive to or mediated by the activated complement system. In some methods, the cellular activity to be modulated is cell lysis. Some methods further comprise detecting the cellular activity by, e.g., a hemolysis assay. In some methods, the cellular activity is detected with urine, blood plasma, serum, whole blood, or eye fluid from the subject.

Figure 1:
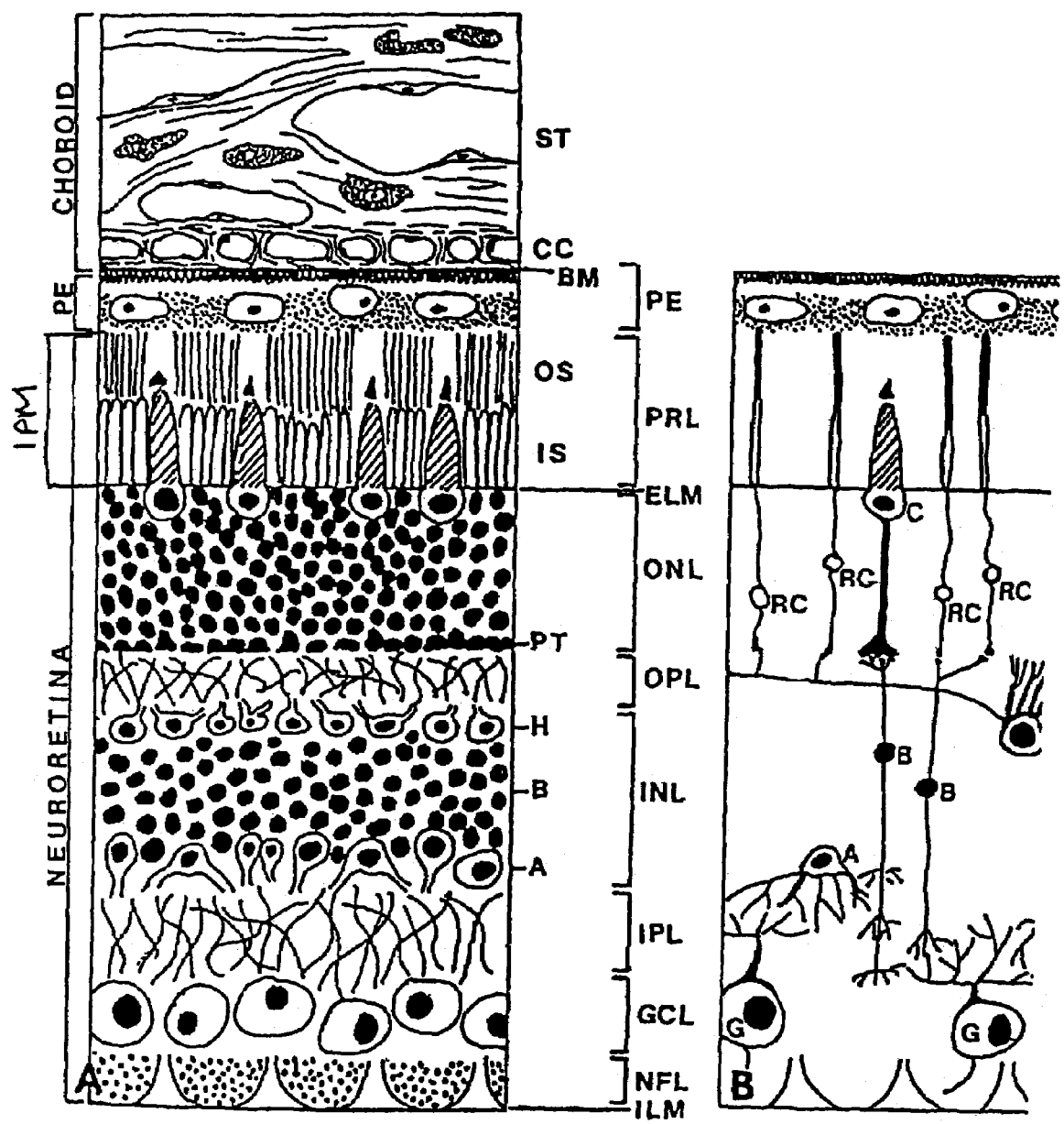
FIG. 1 is a schematic representation of the retina and choroid, as seen in (A) histologic section, and (B) retinal neurons shown diagrammatically. A, amacrine cells; B, bipolar cells; BM, Bruch's membrane; C, cone cells; CC, choriocapillaris; ELM, external limiting membrane; G, ganglion cells; GCL, ganglion cell layer; H, horizontal cells; ILM, inner limiting membrane; INL, internal nuclear layer; IPM, interphotoreceptor matrix; IS, inner segments of rods and cones; IPL, internal plexiform layer, NFL, nerve fiber layer, ONL, outer nuclear layer; OPL, outer plexiform layer; OS, outer segments of rods and cones; PE, pigment epithelium; PRL, photoreceptor layer; PT, photoreceptor cell terminals; R, rod cells; ST, stroma vascularis of choroid.

| | | |
|---|---|---|
| 364-00 | 78 CM | |
| 409-00 | 10 CF | |
| 457-00 | 89 CF | AMD |
| 243-00 | 80 CF | |
| 239-00 | 80 CF | AMD with CNV (choroidal neovascularization) |

DETAILED DESCRIPTION

The present invention provides methods for diagnosis of macular degeneration-related disorders, and for prevention and treatment of such disorders. The invention is predicated in part on the discovery that the complement system is locally active, especially at the RPE-choroid interface in macular degeneration-related disorders. The methods work by detecting an abnormal activity or level associated with at least one complement pathway associated molecule. The presence of abnormal complement activity or abnormal levels in a biological sample from a subject can be indicative of the existence of, or a predisposition to developing, various macular degeneration-related disorders. Such disorders or disease include, e.g., age-related macular disorder (AMD), North Carolina macular dystrophy, Sorsby's fundus dystrophy, Stargardt's disease, pattern dystrophy, Best disease, dominant drusen, and malattia leventinese. Other macular degeneration-related ocular diseases that can be diagnosed or treated with the methods include, e.g., retinal detachment, chorioretinal degenerations, retinal degenerations, photoreceptor degenerations, RPE degenerations, mucopolysaccharidoses, rod-cone dystrophies, cone-rod dystrophies, and cone degenerations.

The methods are suitable for large scale screening of a population of subjects for the presence of these macular degeneration-related disorders, optionally, in conjunction with additional biochemical and/or genetic markers of other disorders that may reside in the subjects. The methods are also suitable for monitoring subjects who have previously been diagnosed with a macular degeneration-related disorder, particularly their response to treatment. Methods of analyzing abnormal complement activities or abnormal levels can be performed in combination, optionally in further combination with detecting other genetic, phenotypic, or genotypic markers correlated with macular degeneration-related disorders or drusen-associated diseases, as described by WO 00/52479. Optionally, analysis of phenotypic markers can be combined with polymorphic analysis of genes encoding complement pathway molecules for polymorphisms correlated with the macular degeneration-related disorders.

The following sections provide guidance for making and using the compositions of the invention, and for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. The following definitions are provided to assist the reader in the practice of the invention.

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "agonist" is an agent that enhances or upregulates (e.g., potentiates or supplements) the production or activity of a gene product. An agonist can also be a compound which increases the interaction of a gene product, molecule or cell with another gene product, molecule or cell, e.g., of a gene product with another homologous or heterologous gene product, or of a gene product with its receptor. A preferred agonist is a compound which enhances or increases binding or activation of a transcription factor to an upstream region of a gene and thereby activates the gene. Any agent that activates gene expression, e.g., by increasing RNA or protein synthesis or decreasing RNA or protein turnover, or gene product activity may be an agonist whether the agent acts directly on the gene or gene product or acts indirectly, e.g., upstream in the gene regulation pathway. Agonists may be RNAs, peptides, antibodies and small molecules, or a combination thereof.

The term "antagonist" is an agent that downregulates (e.g., suppresses or inhibits) the production or activity of a gene product. Such an antagonist can be an agent which inhibits or decreases the interaction between a gene product, molecule or cell and another gene product, molecule or cell. A preferred antagonist is a compound which inhibits or decreases binding or activation of a transcription factor to an upstream region of a gene and thereby blocks activation of the gene. Any agent that inhibits gene expression or gene product activity may be an antagonist whether the agent acts directly on the gene or gene product or acts indirectly, e.g., upstream in the gene regulation pathway. An antagonist can also be a compound that downregulates expression of a gene or which reduces the amount of gene product present, e.g., by decreasing RNA or protein synthesis or increasing RNA or protein turnover. Antagonists may be RNAs, peptides, antibodies and small molecules, or a combination thereof.

The term "antibody" or "immunoglobulin" is used to include intact antibodies and binding fragments thereof. Typically, fragments compete with the intact antibody from which they were derived for specific binding to an antigen fragments including separate heavy chains, light chains Fab, Fab', F(ab')2, Fabc, and Fv. Fragments are produced by recombinant DNA techniques, or by enzymatic or chemical separation of intact immunoglobulins. The term "antibody" also includes one or more immunoglobulin chain that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin Exp. Immunol. 79:315-321 (1990); Kostelny et al., J. Immunol. 148, 1547-1553 (1992).

The term "antisense molecules" include antisense or sense oligonucleotides comprising a single-stranded nucleic acid sequence (either RNA or DNA) capable of binding to target mRNA (sense) or DNA (antisense) sequences for a specific protein (e.g., a complement pathway molecule). The ability to derive an antisense or a sense oligonucleotide, based upon a cDNA sequence encoding a given protein is described in, e.g., Stein and Cohen (Cancer Res. 48:2659, 1988) and van der Krol et al. (BioTechniques 6:958, 1988).

The term "complement activity" broadly encompasses the biochemical and physiological activities associated with the complement system, individual complement pathway associated molecules, as well as genes encoding these molecules. Therefore, complement activities include, e.g., structure and expression of a gene encoding a complement pathway molecule, biochemical activity (e.g., enzymatic or regulatory) of a complement pathway molecule, cellular activities that initiate or result from activation of the complement system, and presence of serum autoantibodies against complement pathway molecules.

The term "complement components" or "complement proteins" refers to the molecules that are involved in activation of the complement system. The classical pathway components include, e.g., C1q, C1r, C1s, C4, C2, C3, C5, C6, C7, C8, C9, and C5b-9 complex (membrane attack complex: MAC). The alternative pathway components include, e.g., Factor B, Factor D, Properdin, H and I. The main lectin pathway component is mannose-binding protein (MBP).

The terms "complement pathway associated molecules," "complement pathway molecules," and "complement pathway associated proteins" are used interchangeably and refer to the various molecules that play a role in complement activation and the downstream cellular activities mediated by, responsive to, or triggered by the activated complement system. They include initiators of complement pathways (i.e., molecules that directly or indirectly triggers the activation of complement system), molecules that are produced or play a role during complement activation (e.g., complement proteins/enzymes such as C3, C5, C5b-9, Factor B, MASP-1, and MASP-2), complement receptors or inhibitors (e.g., clusterin, vitronectin, CR1, or CD59), and molecules regulated or triggered by the activated complement system (e.g., membrane attack complex-inhibitory factor, MACIF; see, e.g., Sugita et al., J Biochem, 106:589-92, 1989). Thus, in addition to complement proteins noted above, complement pathway associated molecules also include, e.g., C3/C5 convertase regulators (RCA) such as complement receptor type 1 (also termed CR1 or CD35), complement receptor type 2 (also termed CR2 or CD21), membrane cofactor protein (MCP or CD46), and C4bBP; MAC regulators such as vitronectin, clusterin (also termed "SP40,40"), CRP, CD59, and homologous restriction factor (HRF); immunoglobulin chains such as Ig kappa, Ig lambda, or Ig gamma); C1 inhibitor, and other proteins such as CR3, CR4 (CD11b/18), and DAF (CD 55).

A "detectable label" refers to an atom (e.g., radionuclide), molecule (e.g., fluorescein), or complex, that is or can be used to detect (e.g., due to a physical or chemical property) the presence of another molecule. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, chemical means and the like.

The term "drusen" refers to deposits that accumulate between the RPE basal lamina and the inner collagenous layer of Bruch's membrane (see, e.g., van der Schaft et al., Ophthalmol. 99: 278-86, 1992; Spraul et al. Arch. Ophthalmol. 115: 267-73, 1997; and Mullins et al., *Histochemical comparison of ocular "drusen" in monkey and human*, In M. LaVail, J. Hollyfield, and R. Anderson (Eds.), in *Degenerative Retinal Diseases* (pp. 1-10). New York: Plenum Press, 1997). Hard drusen are small distinct deposits comprising homogeneous eosinophilic material and are usually round or hemispherical, without sloped borders. Soft drusen are larger, usually not homogeneous, and typically contain inclusions and spherical profiles. Some drusen may be calcified. The term "diffuse drusen," or "basal linear deposit," is used to describe amorphous material which forms a layer between the inner collagenous layer of Bruch's membrane and the retinal pigment epithelium (RPE). This material can appear similar to soft drusen histologically, with the exception that it is not mounded.

The term "drusen-associated disease," or "drusen-associated disorder," refers to any disease in which formation of drusen or drusen-like extracellular disease plaque takes place, and for which drusen or drusen-like extracellular disease plaque causes or contributes thereto or represent a sign thereof. Drusen-associated disease or disorder primarily includes macular degeneration-related disorders wherein drusen is present. But it also encompasses non-ocular age-related diseases with extracellular disease plaques such as amyloidosis, elastosis, dense deposit disease, and/or atherosclerosis. The term also includes glomerulonephritis (e.g., membranous and post-streptococcal/segmental which have associated ocular drusen).

The term "epitope" or "antigenic determinant" refers to a site on an antigen to which B and/or T cells respond B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

The term "fusion protein" refers to a composite polypeptide, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art.

The term "macular degeneration-related disorder" refers to any of a number of conditions in which the retinal macula degenerates or becomes dysfunctional, e.g., as a consequence of decreased growth of cells of the macula, increased death or rearrangement of the cells of the macula (e.g., RPE cells), loss of normal biological function, or a combination of these events. Macular degeneration results in the loss of integrity of the histoarchitecture of the cells and/or extracellular matrix of the normal macula and/or the loss of function of the cells of the macula. Examples of macular degeneration-related disorder include AMD, North Carolina macular dystrophy, Sorsby's fundus dystrophy, Stargardt's disease, pattern dystrophy, Best disease, dominant drusen, and malattia leventinese (radial drusen). The term also encompasses extramacular changes that occur prior to, or following dysfunction and/or degeneration of the macula. Thus, the term "macular degeneration-related disorder" also broadly includes any condition which alters or damages the integrity or function of the macula (e.g., damage to the RPE or Bruch's membrane). For example, the term encompasses retinal detachment, chorioretinal degenerations, retinal degenerations, photoreceptor degenerations, RPE degenerations, mucopolysaccharidoses, rod-cone dystrophies, cone-rod dystrophies and cone degenerations.

The terms "modulation", "alteration", "modulate", or "alter" are used interchangeably herein to refer to both upregulation (i.e., activation or stimulation (e.g., by agonizing or potentiating) and downregulation (i.e., inhibition or suppression (e.g., by antagonizing, decreasing or inhibiting)) of an activity or a biological process (e.g., complement process). "Modulates" or "alters" is intended to describe both the upregulation or downregulation of a process. A process which is upregulated by a certain stimulant may be inhibited by an antagonist to that stimulant. Conversely, a process that is downregulated by a certain stimulant may be inhibited by an antagonist to that stimulant.

By "randomized" is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized proteinaceous test agents. The library can be fully randomized, with no sequence preferences or constants at any position.

"Specific binding" between two entities means an affinity of at least $10^6$, $10^7$, $10^8$, $10^9$ M-1, or $10^{10}$ M-1. Affinities greater than $10^8$ M-1 are preferred.

A "subject" includes both humans and other animals (particularly mammals) and other organisms that receive either prophylactic or therapeutic treatment.

The term "test agent" as used herein describes any molecule, e.g., protein, oligopeptide, small organic molecule, polysaccharide, polynucleotide, etc., that can be screened for their capability of directly or indirectly altering the bioactivities of a complement pathway molecule.

A "variant" refers to a polypeptide amino acid sequence that is altered by one or more amino acid residues relative to the wild type sequence, or a polynucleotide sequence that is altered by one or more nucleotide residue relative to the wild type sequence. Unless otherwise specified, the term "analog" can be used interchangeably with "variant'. A variant can be an allelic variant, a species variant, or an induced variant. The variant can have "conservative" changes, wherein a substituted amino acid has similar structural or chemical properties (e.g., replacement of leucine with isoleucine). Alternatively, a variant can have "nonconservative" changes (e.g., replacement of glycine with tryptophan). Analogous minor variations can also include amino acid deletions or insertions, or both. Guidance in determining which amino acid residues can be substituted, inserted, or deleted without abolishing biological or immunological activity can be found using computer programs well known in the art, for example, LASERGENE™ software.

II. Abnormal Complement Activity in Macular Degeneration-Related Disorders

A. Complement Pathway Molecules in Drusen and Macular Degeneration-related Disorders The complement system and complement components are involved in various immune processes. For example, complement C5b-9 complex, also termed the terminal complex or the membrane attack complex (MAC), plays an important role in cell death by inducing membrane permeability damages. As detailed below in the Examples, the present inventor has discovered that the complement process is associated with the development of drusen and the etiology of macular degeneration-related disorders. Numerous complement pathway proteins including the MAC are found to be associated with drusen, Bruch's membrane, the basal surface of the RPE, and/or the sub-RPE space by immunohistochemical and biochemical studies (Tables 1 and 2). Analyses of drusen composition have revealed the presence of components of the complement system, such as complements 3, 5 and 9, C5b-9 terminal complexes, and C-reactive protein (CRP; a serum protein that plays a role in complement activation and immunomodulation; Volanakis, Ann N Y Acad Sci, 389:235-50; 1982; and Kilpatricket al., J. Immunol., 134: 3364, 1985). The present inventor also discovered that other molecules which are involved in the complement process are also present in drusen, e.g., regulators of complement system including CR1 (Ng et al., Clin Exp Immunol. 71:481-5, 1988) and CR2 (Mold et al., J Immunol. 140:1923-9, 1988), clusterin (a complement inhibitor which binds to complement C7, C8b, and C9; Tschopp et al., J Immunol. 151:2159-65, 1993), vitronectin (also termed "complement S-protein," a complement inhibitor which binds to C5b-7 and C9; Milis et al., Clin Exp Immunol. 92:114-9, 1993), and gp330/megalin (Bachinsky et al., Am J Pathol. 143:598-611, 1993).

Additional complement pathway-associated molecules localized in Bruch's membrane and/or drusen include C3d, C6, C7, C8, C9, Factor D, Factor H, Factor L Factor B, clusterin, and mannose binding protein. Further, some complement pathway-associated molecules such as CD21, CD35, CD55/decay accelerating factor, and CD59/protectin, are present in the basal surface of the RPE.

In addition, data from differential gene expression analyses indicate a significant downregulation of complement pathway molecules (e.g., complement 6, clusterin) and up-regulation of a number of immune system-associated molecules (including Ig mu, lambda, J, and kappa chains) in the RPE/choroid of AMD donors, as compared to age-matched controls (see, e.g., Example 5).

Another indicator of abnormal complement activity is the presence or increased levels of autoantibodies against various macular degeneration-associated autoantigens. Some autoantibodies have been detected in the sera of AMD subjects (Guerne et al., Ophthalmology, 1991. 98: 602-7; Penfold et al., Clin. Exp. Ophthalmol., 1990. 228: 270-4). Further macular degeneration-associated autoantigens identified by the present inventors include complement pathway molecules and various proteins from RPE, choroid, and retina. As discussed in the Examples, autoantibodies against these macular degeneration-associated autoantigens were found in serum of patients with macular degeneration-related disorders (e.g., AMD and Malattia Leventinese). Examples of autoantibodies against complement pathway associated molecules include autoantibodies against vitronectin (Example 10). Examples of autoantibodies against RPE, choroid, or retina proteins include autoantibodies against β crystallin (A2, A3, A4, and S), calreticulin, 14-3-3 protein epsilon, serotransferrin, albumin, keratin, pyruvate carboxylase, villin 2 (example 11), as well as a number of other proteins (Example 12).

As discussed in the Examples, infra, detection of autoantibodies against complement pathway molecules or against RPE, choroid, or retina components provides another means for diagnosing and treating macular degeneration-related disorders (e.g., AMD). In addition, the specific genetic loci that cause macular degeneration-related disorders (e.g., AMD) can be identified by further analysis and identification of the various macular degeneration-associated antoantigens.

Taken together, these data indicate that the complement system plays an important role in drusen development and the etiology of macular degeneration-related disorders (e.g., AMD).

B. Correlation Between Complement Activity in the RPE-choroid Interface and Macular Degeneration Significantly, the present inventors also discovered that a number of messengers for the complement pathway associated molecules detected in drusen and Bruch's membrane are produced locally by specific ocular cells (see, e.g., Examples 3 and 4). These molecules include, e.g., complements 3, 5 and 9, CRP, immunoglobulin lambda and kappa light chains, Factor X, HLA-DR, apolipoprotein A, apolipoprotein E, amyloid A, and vitronectin. For example, C3 and C5 are synthesized by the RPE as are APP, clusterin, and Factor H. A number of other complement components that are not synthesized by the RPE, such as C9 and MASP-1, are synthesized by adjacent choroidal and/or retinal cells and could therefore contribute to complement activation in Bruch's membrane. These data indicate a role for locally produced complement components in the activation of complement in Bruch's membrane and, possibly, in the etiology of macular degeneration-related disorders.

The present inventor has also discovered that there is a strong correlation between intensity and distribution of complement components (e.g., C5b-9 complex) in the RPE-choroid (especially in the interface) and AMD (see, e.g., Example 2). Significantly, intense labeling of the entire choriocapillaris (endothelium, pericytes, and associated extracellular matrix) was observed in donors with AMD (9 of 10 donors), as compared to older, age-matched donors without a diagnosis of AMD (2 of 10 donors). When combined with the observation that C5b-9 complexes are associated with RPE and choroidal cell membranes, these data indicate that the choriocapillaris of AMD subjects can be under more rigorous attack than that of individuals without AMD. Also, the distribution of immunoreactive C5b-9 and detectable levels of C5b-9 in the samples from AMD donors indicate that complement pathway inhibitors such as clusterin, vitronectin CD56 and CD55 may fail to suppress the terminal pathway, thereby permitting formation of MAC.

Complement-mediated damage to the choriocapillaris can lead to abnormal responses by the choroid (e.g., inflammation, cytokine secretion, neovascularization) and/or choriocapillaris cell death. These events, in turn, can lead to further dysfunction and death of surrounding cells, including the RPE and choroid, and the biogenesis of drusen. Indeed, the present inventors have discovered that MAC is inserted into the cell membranes of both choroidal and RPE cells (see, e.g., Examples 2 and 3). Similar processes are also active in other diseases, including atherosclerosis and Alzheimer disease.

These data also provide evidence that Bruch's membrane can serve as an unusual activating surface for complement in its physiologically "normal" state, and that activated C5b-9 is poorly cleared from Bruch's membrane compared with other structures in the healthy choroid. It is clear that complement activation occurs at the RPE-choroid interface chronically, and that a strong correlation between intensity and distribution of C5b9 associated with the choriocapillaris and AMD exists. As discussed below, the present invention provides novel diagnostics and therapeutics for macular degeneration-related disorders in accordance with such discovery.

III. Diagnostics: Abnormal Complement Activity in Macular Degeneration-related Disorders The present invention provides methods for diagnosing, or determining a predisposition to development of, a macular degeneration-related disorder by detecting abnormal levels or abnormal activities of complement pathway associated molecules, or abnormal cellular activities associated with complement pathways. The complement pathway-associated molecules include initiators of complement pathways, i.e., any molecule which directly or indirectly triggers the activation of complement system through any of the three complement pathways, such as autoantigens, autoantibodies, immune complexes, or MBL. They also include molecules that are produced or play a role during complement activation, e.g., complement proteins/enzymes (e.g., C3, C5, C5b-9, Factor B, MASP-1, and MASP-2) and receptors or inhibitors (e.g., vitronectin, CR1, and vitronectin). Further, the complement pathway associated molecules that can be diagnosed with methods of the present invention also include molecules that regulated by the activated complement system (e.g., MACIF). Cellular activities regulated by the activated complement system include, e.g., cell damage resulting from the C5b-9 attack complex, vascular permeability changes, contraction and migration of smooth muscle cells, T cell proliferation, immune adherence, aggregation of dendritic cells, monocytes, granulocyte and platelet, phagocytosis, migration and activation of neutrophils (PMN) and macrophages. The diagnostic methods of the present invention encompass detection of abnormality in any of these complement pathway associated molecules or cellular activities. Further, the diagnostic methods of the present invention are also directed to detecting abnormal levels of activities of molecules that are directly up-regulated or down-regulated by the complement system.

Typically, a diagnostic test works by comparing a measured level of at least one complement pathway molecule (expression level or a biochemical activity) in a subject with a baseline level determined in a control population of subjects unaffected by a macular degeneration-related disorder. If the measured level does not differ significantly from baselines levels in a control population, the outcome of the diagnostic test is considered negative. On the other hand, if there is a significant departure between the measured level in a subject and baseline levels in unaffected subjects, it signals a positive outcome of the diagnostic test, and the subject is considered to have an abnormal level or activity of that complement pathway molecule.

A departure is considered significant if the measured value falls outside the range typically observed in unaffected subjects due to inherent variation between subjects and experimental error. For example, in some methods, a departure can be considered significant if a measured level does not fall within the mean plus one standard deviation of levels in a control population. Typically, a significant departure occurs if the difference between the measured level and baseline levels is at least 20%, 30%, or 40%. Preferably, the difference is by at least 50% or 60%. More preferably, the difference is more than at least 70% or 80%. Most preferably, the difference is by at least 90%. The extent of departure between a measured value and a baseline value in a control population also provides an indicator of the probable accuracy of the diagnosis, and/or of the severity of the disease being suffered by the subject.

Various biological samples from a subject can be used for the detection, e.g., samples obtained from any organ, tissue, or cells, as well as blood, urine, or other bodily fluids (e.g., eye fluid),. For some diagnostic methods, a preferred sample is eye fluid. For some other methods, a preferred tissue sample is whole blood and products derived therefrom, such as plasma and serum. Blood samples can be obtained from blood-spot taken from, for example, a Guthrie card. Other sources of tissue samples are skin, hair, urine, saliva, semen, feces, sweat, milk, amniotic fluid, liver, heart, muscle, kidney and other body organs. Others sources of tissue are cell lines propagated from primary cells from a subject. Tissue samples are typically lysed to release the protein and/or nucleic acid content of cells within the samples. The protein or nucleic acid fraction from such crude lysates can then be subject to partial or complete purification before analysis.

In some methods, multiple diagnostic tests for multiple markers are performed on the same subject. Typically, multiple tests are performed on different aliquots of the same biological sample. However, multiple assays can also be performed on separate samples from the same tissue source, or on multiple samples from different tissue sources. For example, a test for one marker can be performed on a plasma sample, and a test for a second marker on a whole blood-sample. In some methods, multiple samples are obtained from the same subject at different time points. In such methods, the multiple samples are typically from the same tissue, for example, all serum.

A. Diagnosing Abnormal Levels of Complement Pathway Molecules

The present invention provides methods for detecting abnormal levels of complement pathway associated molecules that are indicative of the presence or a predisposition to development of a macular degeneration-related disorder. Either abnormal levels of complement pathway-associated proteins or abnormal levels of mRNAs encoding the complement pathway-associated proteins can be detected. For example, abnormal levels of complement proteins (e.g., C6, C3, C5, C6) or other complement pathway molecules (e.g., clusterin, CRP, or Ig chains) could be indicative of a disease state or a predisposition to developing a macular degeneration-related disorder (e.g., AMD). Either abnormal mRNA levels or abnormal protein levels can be detected. The abnormal expression can be either upregulation or downregulation.

To detect abnormal protein levels of the complement pathway associated molecules, various immunohistochemical and biochemical assays can be used. For example, levels of the complement components or split products generated in the activation of the alternative or classical pathway can be measured as described, e.g., in Buyon et al., Arthritis Rheum, 35:1028-37, 1992 (e.g., plasma levels of Ba, Bb, SC5b-9, and C4d); Langlois et al., J Allergy Clin Immunol, 83:11-6,1989 (serum levels of C3a, C4a, C5a, C1rC1s-C1-inhibitor complex, and terminal C complex C5b9), and Caraher et al., J Endocrinol 162:143-53, 1999. These methods can be readily employed to detect body fluid concentration of any complement pathway associated protein in a subject suspected to have or to develop a specific macular degeneration-related disorder. As controls, expression levels of the complement pathway-associated protein are also measured for subjects who respectively have or do not have the specific macular degeneration-related disorder.

For mRNAs encoding complement pathway molecules, there are a number of methods available for detecting abnormal levels in a biological sample from a subject. Nucleic acids obtained from a biological sample of the subject can be amplified first. Amplification techniques are known to those of skill in the art and include, but are not limited to cloning, polymerase chain reaction (PCR), polymerase chain reaction of specific alleles (ASA) ligase chain reaction (LCR), nested polymerase chain reaction, self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), and Q-Beta Replicase (Lizardi, P. M. et al., 1988, Bio/Technology 6:1197).

To determine gene expression level of a given complement pathway associated molecule, methods routinely practiced in the art, such as a differential display procedure, Northern analysis, RT-PCR, and DNA probe arrays, can be employed to detect the expression level of a given complement pathway associated in a subject Fingerprint profiles of expression levels of a number of complement pathway associated molecules, or of expression levels of a given complement pathway associated molecule in a population of control subjects with or without macular degeneration-related disorders, can be generated using methods described in the art e.g., WO99/23254; and Cronin et al. Human Mutation 7:244, 1996.

B. Diagnosing Variant Form of Nucleic Acids Encoding Complement Pathway Molecules or Autoantigens The present invention provides methods for diagnosing, or determining a predisposition to development of, a macular degeneration-related disorder by detecting a variant form of at least one nucleic acid molecule encoding a complement pathway associated molecule or an autoantigen (e.g., RPE proteins, choroidal proteins, retinal proteins, or autoantigens from other tissues that bind to the ocular tissues). The nucleic acids can be, e.g., genomic DNA, cDNA, or mRNA. Compared to the wild-type nucleic acid sequence, the variant nucleic acid can have point mutations, frameshift mutations, or deletions. In some methods, the variant nucleic acid can have the wild-type sequence except for a single nucleotide polymorphism.

A variety of means are currently available for detecting variant genes or nucleic acids. For example, many methods are available for detecting specific alleles at human polymorphic loci. For example, single nucleotide polymorphism in complement pathway genes can be detected as described, e.g., in Mundy et al., U.S. Pat. No. 4,656,127; Cohen et al., French Patent 2,650,840; and WO91/02087). Additional procedures for assaying polymorphic sites in DNA have been described in Komher, J. S. et al., Nucl. Acids. Res. 17:7779-7784 (1989); Sokolov, B. P., Nucl. Acids Res. 18:3671 (1990); Syvanen, A. -C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)).

Other suitable techniques to detect variant nucleic acids encoding oligonucleotide ligation assay (OLA), as described, e.g., in U.S. Pat. No. 4,998,617 and Landegren, U. et al. ((1988) Science 241:1077-1080); or selective oligonucleotide hybridization as described, e.g., in Saiki et al. (1986) Nature 324:163); and Saiki et al (1989) Proc. Natl Acad. Sci USA 86:6230). For mutations that produce premature termination of protein translation, the protein truncation test (PTT) offers an efficient diagnostic approach (Roest, et. al., (1993) Hum. Mol. Genet 2:1719-21; van der Luijt, et. al., (1994) Genomics 20:1-4). Mismatched bases in RNA/RNA or RNA/DNA or DNA/DNA heteroduplexes can be detected as described, e.g., in Myers, et al., Science 230:1242, 1985.

In addition, a variety of sequencing reactions can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures can be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159).

Any cell type or tissue can be utilized to obtain nucleic acid samples for use in the diagnostics described herein. For example, a DNA sample is obtained from blood, a bodily fluid (e.g., secretion from the eye), urine, or saliva. In some methods, samples obtained from the eyes are preferred because test results obtained from a sample from the eye evidence that an abnormal expression or activity is likely due to an ocular dysfunction, e.g., macular degeneration, thereby providing a more rapid and accurate diagnostic test for macular degeneration-related disorders. In some methods, nucleic acid tests can be performed on dry samples (e.g. hair or skin). The diagnostic methods can also be performed in situ directly upon tissue sections (fixed and/or frozen) of subject tissue obtained from biopsies or resections, such that no nucleic acid purification is necessary. Nucleic acid reagents may be used as probes and/or primers for such in situ procedures (see, e.g., Nuovo et al., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated as described.

The present invention also provides kits for detecting a predisposition for developing a macular degeneration-related disorder. This kit may contain one or more oligonucleotides, including 5' and 3' oligonucleotides that hybridize 5' and 3' to at least one complement pathway molecule. The assay kits and diagnostic methods can also employ labeled oligonucleotides to allow ease of identification in the assays. Examples of labels which may be employed include radiolabels, enzymes, fluorescent compounds, streptavidin, avidin, biotin, magnetic moieties, metal binding moieties, antigen or antibody moieties, and the like.

C. Diagnosing Abnormal Activity of Complement System

The present invention also provides methods for diagnosing, or determining a predisposition to developing a macular degeneration-related disorder by detecting an abnormal bioactivity of the complement system. The abnormal activities to be detected can be that which triggers the activation of each of the three complement pathways. The abnormal activity can also be that of individual molecules which are produced during activation of the three complement pathways. The abnormal complement activities to be detected can also be any of the cellular activities displayed by the activated complement system. Thus, abnormal complement activities to be detected with the present invention encompass, e.g., increased or decreased enzymatic or regulatory function of a complement pathway protein such as C3a, C5a, C5b-9 complex, vitronectin, or CR1, serum presence or increased level of autoantibodies against complement component, abnormal cellular activities mediated by activated complement system such as lysis of target cells (e.g., RPE and choroidal cells), chemotaxis, opsonization, stimulation of vascular and other smooth muscle cells, degranulation of mast cells, increased permeability of small blood vessels, initiation of inflammatory processes, directed migration and activation of leukocytes, and activation of B lymphocytes, macrophages, dendritic cells, and neutrophils.

With respect to each complement bioactivity, abnormality refers to a difference between that activity detected in a biological sample (e.g., blood) from a test subject and the average value of the activity detected in a population of control subjects without macular degeneration-related disorders. Preferably, the difference is by at least 20%, 30%, or 40%. More preferably, the difference is more than at least 50%, 60%, 70%, or 80%. Most preferably, the difference is by at least 90%.

1. Detecting Complement Activation

Various methods can be used to measure activities of complement pathway molecules and activation of the complement system (see, e.g., U.S. Pat. No. 6,087,120; and Newell et al., J Lab Clin Med, 100:437-44,1982). For example, the complement activity can be monitored by (i) measurement of inhibition of complement-mediated lysis of red blood cells (hemolysis); (ii) measurement of ability to inhibit cleavage of C3 or C5; and (iii) inhibition of alternative pathway mediated hemolysis.

The two most commonly used techniques are hemolytic assays (see, e.g., Baatrup et al., Ann Rheum Dis, 51:892-7, 1992) and immunological assays (see, e.g., Auda et al., Rheumatol Int, 10:185-9, 1990). The hemolytic techniques measure the functional capacity of the entire sequence-either the classical or alternative pathway. Immunological techniques measure the protein concentration of a specific complement component or split product. Other assays that can be employed to detect complement activation or measure activities of complement components in the methods of the present invention include, e.g., T cell proliferation assay (Chain et al., J Immunol Methods, 99:221-8, 1987), and delayed type hypersensitivity (DTH) assay (Forstrom et al., 1983, Nature 303:627-629; Hallidayet al., 1982, in *Assessment of Immune Status by the Leukocyte Adherence Inhibition Test*, Academic, New York pp. 1-26; Koppi et al., 1982, Cell. Immunol. 66:394-406; and U.S. Pat. No. 5,843,449).

In hemolytic techniques, all of the complement components must be present and functional. Therefore hemolytic techniques can screen both functional integrity and deficiencies of the complement system (see, e.g., Dijk et al., J Immunol Methods 36: 29-39, 1980; Minh et al., Clin Lab Haematol. 5:23-34 1983; and Tanaka et al., J Immunol 86: 161-170, 1986). To measure the functional capacity of the classical pathway, sheep red blood cells coated with hemolysin (rabbit IgG to sheep red blood cells) are used as target cells (sensitized cells). These Ag-Ab complexes activate the classical pathway and result in lysis of the target cells when the components are functional and present in adequate concentration. To determine the functional capacity of the alternative pathway, rabbit red blood cells are used as the target cell (see, e.g., U.S. Pat. No. 6,087,120).

The hemolytic complement measurement is applicable to detect deficiencies and functional disorders of complement proteins, e.g., in the blood of a subject, since it is based on the function of complement to induce cell lysis, which requires a complete range of functional complement proteins. The so-called CH50 method, which determines classical pathway activation, and the AP50 method for the alternative pathway have been extended by using specific isolated complement proteins instead of whole serum, while the highly diluted test sample contains the unknown concentration of the limiting complement component. By this method a more detailed measurement of the complement system can be performed, indicating which component is deficient.

Immunologic techniques employ polyclonal or monoclonal antibodies against the different epitopes of the various complement components (e.g., C3, C4 an C5) to detect, e.g., the split products of complement components (see, e.g., Hugli et al., Immunoassays Clinical Laboratory Techniques 443-460, 1980; Gorski et al., J Immunol Meth 47: 61-73, 1981; Linder et al., J Immunol Meth 47: 49-59, 1981; and Burger et al., J Immunol 141: 553-558, 1988). Binding of the antibody with the split product in competition with a known concentration of labeled split product could then be measured. Various assays such as radio-immunoassays, ELISA's, and radial diffusion assays are available to detect complement split products.

The immunologic techniques provide a high sensitivity to detect complement activation, since they allow measurement of split-product formation in blood from a test subject and control subjects with or without macular degeneration-related disorders. Accordingly, in some methods of the present invention, diagnosis of a macular degeneration-related disorder is obtained by measurement of abnormal complement activation through quantification of the soluble split products of complement components (e.g., C3a, C4a, C5a, and the C5b-9 terminal complex) in blood plasma from a test subjects. The measurements can be performed as described, e.g., in Chenoweth et al., N Engl J Med 304: 497-502, 1981; and Bhakdi et al., Biochim Biophys Acta 737: 343-372, 1983. Preferably, only the complement activation formed in vivo is measured. This can be accomplished by collecting a biological sample from the subject (e.g., serum) in medium containing inhibitors of the complement system, and subsequently measuring complement activation (e.g., quantification of the split products) in the sample.

2. Detecting Autoantibodies to Macular Degeneration-associated Autoantigens or Immune Complexes Abnormal presence or increased level of autoantibodies against tissue specific antigens, neoantigens, and/or complement pathway molecules can also be an indicator of a predisposition of development of macular degeneration-related disorders. Accordingly, the present invention provides methods for diagnosing, or determining a predisposition to development of, a macular degeneration-related disorder by detecting autoantibodies against macular degeneration-associated autoantigens. The diagnostic methods of the present invention are also directed to detecting in a subject circulating immune complexes that can also be indicative of a macular degeneration-related disorder.

As discussed above, autoantibodies against various macular degeneration-associated autoantigens were found in serum from subjects with macular degeneration-related disorders. Such autoantigens include complement pathway molecules and various autoantigens from RPE, choroid, and retina. Thus, diagnosis can be directed to serum autoantibodies against macular degeneration-associated autoantigens such as vitronectin, β crystallin, calreticulin, serotransferrin, keratin, pyruvate carboxylase, C1, and villin 2. For example, in some methods, a blood sample (e.g., serum) from a test subject can be examined for specific binding to these known autoantigens. In some methods, the sample is examined for specific binding to any autoantigens from the ocular tissues (e.g., RPE, choroid) using proteins extracted from the ocuclar tissues. For example, proteins extracted from ocular tissues from non-human animals (e.g., rat) or from deceased human beings can be used to screen for autoantibodies against ocular autoantigens in a serum from the subject.

In some methods, the diagnosis also include detection of autoantibodies against neoantigens. Neoantigens are antigens resulting from modification and/or crosslinking of existing molecules by various processes such as oxidation. Examples of neoantigens include neoantigens associated with oxidized LDL in atherosclerosis (Reaven et al., Adv Exp Med Biol, 366(-HD-):113-28, 1994; Kita et al., Ann N Y Acad Sci, 902(-HD-):95-100, 2000), or oxidation-derived complex in other diseases (Ratnoff et al., Am J Reprod Immunol, 34:72-9 1995; and Debrock et al., FEBS Lett, 376:243-6, 1995). Further, detection of autoantibodies against autoantigens from other tissues can be indicative of a systemic nature of that macular degeneration-related disorder.

A number of biochemical or immunochemical techniques can be readily employed to detect autoantibodies in a biological sample from a subject. For example, techinques routinely praticed in the art such as immunoprecipitation or radioimmune assays are suitable for detecting autoantibodies in a serum sample. Various other methods for detection of autoantibodies against complement proteins or complement regulatory proteins have been described in the art. For example, Pinter et al. described detection of autoantibodies against two complement regulatory molecules expressed in the membrane of human cells (CD46 and CD59) in sera from subjects with multiple sclerosis (J Neurovirol, 6 Suppl 2:S42-6, 2000). Strife et al. described detection of serum autoantibodies to C3 convertases C3bBb and C3bBbP in membranoproliferative glomerulonephritis (J Pediatr. 116: S98-102, 1990). Ravelli et al. disclosed autoantibodies to complement C1q in subjects with pediatric-onset systemic lupus erythematosus (Clin Exp Rheumatol. 15:215-9, 1997). As discussed in the Examples, infra, these methods can be readily applied to detect autoantibodies against of complement components, e.g., in the serum from a subject suspected to have an macular degeneration-related disorder.

Significance of circulating immune complexes are well documented in the art. For example, the causative mechanism for glomerulonephritis is typically the deposit of circulating immune complexes in the kidney (see, e.g., U.S. Pat. No. 6,074,642). Circulating immune complexes as a result of activation and consumption of individual complement components have also been shown in many other human diseases occurs (see, e.g., U.S. Pat. No. 5,221,616). Detection of circulating immune complexes also can be of diagnostic value in macular degeneration related disorders. A number of assays are routinely practiced to detect circulating immune complexes in a subject, e.g., as described in Tomimori-Yamashita et al., Lepr Rev, 70(3):261-71, 1999 (antibody-based enzyme-linked immunosorbent assay); Krapf et al., J Clin Lab Immunol, 21(4):183-7, 1986 (fluorescence linked immunosorbent assay); Kazeem et al., East Afr Med J, 67(6):396-403, 1990 (laser immunonephelometry); and Rodrick et al., J Clin Lab Immunol, 7(3):193-8, 1982 (Protein A-glass fiber filter assay, PA-GFF, and polyethylene glycol insolubilization assay). Each of these well known assays can be employed to detect circulating immune complexes for the methods of the present invention.

D. Additional Tests for Diagnosing Macular Degeneration-Related Disorders

If a diagnostic test described above gives a positive outcome, the subject is, at minimum, identified as being susceptible to or at risk of a macular degeneration-related disorder. The subject is then typically subject to further tests or screening. For example, the present inventors have found that there is a correlation between macular degeneration and the distribution of the C5b-9 complex in choriocapillaris. Thus, the additional tests or screening can include examination of the function or physical integrity of an ocular tissue of the subject's eyes (e.g., choriocapillaris) by one of the ophthalmologic procedures described below. The additional tests or screening can also include analyses of additional complement pathway molecules that have not already been tested. The additional tests can also include examination of the presence of macular degeneration-associated genetic markers, drusen-associated phenotypic markers, or drusen-associated genotypic markers that often correlate with macular degeneration-related disorders, as discussed below.

Macular degeneration-associated genetic markers are genetic loci which are shown to be correlated with a risk of developing a macular degeneration-related disorder. Such markers have been described, e.g., in WO 00/52479, and include, e.g., 1p21-q13, for recessive Stargardt's disease or fundus flavi maculatus (Allikmets et al. Science 277:1805-1807, 1997); 1q25-q31, for recessive AMD (Klein et al., Arch. Ophthalmol. 116:1082-1088, 1988); 2p16, for dominant radial macular drusen, dominant Doyne honeycomb retinal degeneration, or Malattia Leventinese (Edwards et al., Am. J. Ophthalmol. 126:417-424, 1998); 6p21.2-cen, for dominant macular degeneration, adult vitelloform (Felbor et al. Hum. Mutat. 10:301-309, 1997); 6p21.1 for dominant cone dystrophy (Payne et al. Hum. Mol. Genet 7:273-277, 1998); 6q, for dominant cone-rod dystrophy (Kelsell et al. Am. J. Hum. Genet. 63:274-279, 1998); 6q11-q15, for dominant macular degeneration, Stargardt's-like disease (Griesinger et al., Am. J. Hum. Genet. 63:A30, 1998); 6q14-q16.2, for dominant macular degeneration, North Carolina Type (Robb et al., Am. J. Ophthalmol. 125:502-508, 1998); 6q25-q26, dominant retinal cone dystrophy 1 ((http://www3.ncbi.nlm.nih.gov/omim, (1998)); 7p21-p15, for dominant cystoid macular degeneration (Inglehearn et al., Am. J. Hum. Genet. 55:581-582, 1994); 7q31.3-32, for dominant tritanopia, protein: blue cone opsin (Fitzgibbon et al., Hum. Genet. 93:79-80, 1994); 11p12-q13, for dominant macular degeneration, Best type (bestrophin) (Marquardt et al., Hum. Mol. Genet. 7:1517-1525, 1998); 13q34, for dominant macular degeneration, Stargardt type (Zhang et at., Arch. Ophthalmol. 112:759-764, 1994); 16p12.1, for recessive Batten disease (Munroe et al., Am. J. Hum. Genet. 61:310-316, 1997); 17p, for dominant areolar choroidal dystrophy (Lotery, A. J. et al., Ophthalmol. Vis. Sci. 37:1124, 1996); 17p13-p12, for dominant cone dystrophy, progressive (Small et al., Am. J. Ophthalmol. 121:13-18, 1996); 17q, for cone rod dystrophy (Klystra, J. A. et al., Can J. Ophthalmol. 28:79-80, 1993); 18q21.1-q21.3, for cone-rod dystrophy, de Grouchy syndrome (Manhant, S. et al., Am. J. Hum. Genet. 57:A96, 1995; Warburg, M. et al., Am. J. Med. Genet. 39:288-293, 1991); 19q13.3, for dominant cone-rod dystrophy; recessive, dominant and 'de novo' Leber congenital amaurosis; dominant RP; protein: cone-rod otx-like photoreceptor homeobox transcription factor (Li et al., Proc. Natl. Acad. Sci USA 95:1876-1881, 1998); 22q12.1-q13.2, for dominant Sorsby's fundus dystrophy, tissue inhibitors of metalloproteases-3 (TIMP3) (Felbor et al., Am. J. Hum. Genet. 60:57-62, 1997); and Xp11.4, for X-linked cone dystrophy (Seymour et J. Hum. Genet. 62:122-129, 1998).

Drusen-associated phenotypic or genotypic markers that correlate with macular degeneration-related disorders or drusen associated disorders have been described in WO 00/52479. Examples of drusen-associated phenotypic markers include: RPE dysfunction and/or death, immune mediated events, dendritic cell activation, migration and differentiation, extrusion of the dendritic cell process into the sub RPE space (e.g. by detecting the presence or level of a dendritic cell marker such as CD68, CD1a and S100), the presence of geographic atrophy or disciform scars, the presence of choroidal neovascularization and/or choroidal fibrosis, especially in the macula. Examples of drusen-associated genotypic markers include mutant genes and/or a distinct pattern of differential gene expression. Genes expressed by dysfunctional and/or dying RPE cells include: HLA-DR, CD68, vitronectin, apolipoprotein E, clusterin and S-100. Genes expressed by choroidal and RPE cells in AMD include heat shock protein 70, death protein, proteasome, Cu/Zn superoxide dismutase, cathepsins, and death adaptor protein RAIDD. Other markers involved in immune mediated events associated with drusen formation include: autoantibodies (e.g. directed against drusen, RPE and/or retina components), leukocytes, dendritic cells, myofibroblasts, type VI collagen, and a cadre of chemokines and cytokines. In addition to complement proteins, other molecules associated with drusen include: immunoglobulins, amyloid A, amyloid P component, HLA-DR, fibrinogen, Factor X, prothrombin, C reactive protein (CRP) apolipoprotein A, apolipoprotein E, antichymotrypsin, thrombospondin, and vitronectin. Markers of drusen associated dendritic cells include: CD1a, CD4, CD14, CD68, CD83, CD86, and CD45, PECAM, MMP14, ubiquitin, and FGF. Important dendritic cell-associated accessory molecules that participate in T cell recognition include ICAM-1, LFA1, LFA3, and B7, IL-1, IL-6, IL-12, TNFα, GM-CSF and heat shock proteins. Markers associated with dendritic cell expression include: colony stimulating factor, TNFα, and IL-1. Markers associated with dendritic cell proliferation include: GM-CSF, IL4, IL-3, SCF, FLT-3 and TNFα. Markers associated with dendritic cell differentiation include IL-10, M-CSF, IL-6 and IL-4. Markers of fibrosis include: a decrease in BIG H3, increase in β1-integrin, increase in collagen (e.g. collagen 6 α2 and collagen 6 α3), increase in elastin, and an increase in human metallo elastase (HME).

The other phenotypic or genotypic markers can be detected with assays described above, e.g., detection of the identity, expression level, or activities of the gene, mRNA transcript, or encoded protein. Some markers can also be detected by one or more ophthalmologic procedures, such as fundus fluorescein angiography (FFA), indocyanine green angiography (ICG), fundus ophthalmoscopy or photography (FP), electroretinogram (ERG), electrooculogram (EOG), visual fields, scanning laser ophthalmoscopy (SLO), visual acuity measurements, dark adaptation measurements or other standard method. Ophthalmologic procedures have been used to evaluate patients with various macular degeneration-related disorders. For example, Spraul et al. (Klin Monatsbl Augenheilkd, 21:141-8, 1998) described the use of optical coherence tomography for evaluation of patients with AMD; Kohno et al. (Bull Soc Belge Ophthalmol, 259(-HD-):81-8, 1995) reports detection of choroidal neovascularization in age-related macular degeneration using subtraction methods in indocyanine green angiography; Kuck et al. (Retina, 13:36-9, 1993) discussed examination of patients with exudative age-related macular degeneration and clinical signs of subretinal neovascular membranes were examined by scanning laser fluorescein angiography; Kaluzny et al. (Klin Oczna, 101:355-9, 1999) and Yuzawa et al. (Eur J Ophthalmol, 2:115-21, 1992) described the use of indocyanine green (ICG) angiography in diagnosis of occult choroidal neovascularization in age-related macular degeneration; Lubinski et al. (Klin Oczna, 100:263-8, 1998) reported evaluation of foveal cone function in healthy subjects and patients with different macular diseases with foveal cone electroretinogram (FCERG, a type of focal ERG); and Kakehashi et al. (Jpn J Ophthalmol, 40:116-22, 19960 discussed differential diagnosis of macular breaks using the scanning laser ophthalmoscope (SLO). All these procedures can be used in conjunction with the diagnostic methods of the present invention. For instance, fundus autofluorescein angiography can be used for identifying defects at the level of the RPE (see, e.g., Delori et al., Invest Ophthalmol, 14:487-92, 1975; Holz et al., Graefes Arch Clin Exp Ophthalmol, 237:145-52, 1999; and Delori et al., Invest Ophthalmol Vis Sci, 36:718-29, 1995).

Further tests or screening can also include monitoring for clinical symptoms of a macular degeneration-related disorder, which include presence of drusen, retinal pigmentary changes, and includes early stages of degeneration of the macula in which vision has not been significantly affected ("dry" macular degeneration), atrophic macular degeneration, and exudative disease in which neovascularization is prevalent ("wet" macular degeneration). Further screening can also include analyses of family history for related family members with macular degeneration-related disorders, and/or genetic analyses of polymorphisms associated with macular degeneration-related disorders (as described above). As a result of one or more of these additional tests, the initial diagnosis based on abnormal complement activities or expression levels can be confirmed (or otherwise), and the particular type of macular degeneration-related disorder affecting a subject can be identified.

IV. Therapeutics: Prevention and Treatment of Macular Degeneration-related Disorders The present invention provides methods for treating or preventing macular degeneration-related disorders in a subject by administering to the subject therapeutic agents that modulate activity of the complement system. Detrimental nonspecific activation of the complement system, or unfavorable activation by the alternative pathway, can be prevented or treated by therapeutic agents of the invention. For example, as discussed above, the choriocapillaris was implicated as a target of MAC attack in AMD patients, and MAC is present in choroidal and RPE cell membranes. Accordingly, in some methods, therapeutic agents are directed to prevention or alleviation of damages to the choriocapillaris and/or RPE caused by the C5b-9 complex. In some methods, the treatment is directed to inhibition of the formation of the C5b-9 membrane-attack complex using, e.g., inhibitors such as vitronectin or clusterin, or a monoclonal antibody to the complement component C8 alpha subunit (see, e.g., Abraha et al., A; Biochem J, 264:933-6, 1989).

The therapeutics of the present invention are directed to complement pathway associated molecules as well as cellular activities regulated by the activated complement system. Thus, targets of the therapeutic agents of the present invention can include any of the initiators of complement pathways (e.g., autoantibodies), molecules produced during complement activation, molecules produced or differentially regulated as a result of complement activation, regulators of complement pathways, and molecules regulated by the activated complement system (e.g., MACIF). The therapeutic agents can also be used to modulate cellular activities (biologic or immune functions) directly or indirectly mediated by the complement system. Thus, the therapeutic agents of the invention can be directed to cellular activities such as lysis of target cells, chemotaxis, opsonization, stimulation of vascular cells, degranulation of mast cells, increased permeability of small blood vessels, directed migration of leukocytes, and activation of B lymphocytes, macrophages, dendritic cells, monocytes, and neutrophils. These cellular functions can be either antagonized or agonized with therapeutic agents of the present invention.

A. General Considerations

Subjects amenable to treatment include those who are presently asymptomatic but who are at risk of developing a symptomatic macular degeneration-related disorder at a later time. For example, human individuals include those having relatives who have experienced such a disease, and those whose risk is determined by analysis of genetic or biochemical markers, by biochemical methods, or by other assays such as T cell proliferation assay (as described above).

Other subjects who are amenable to treatment include individuals free of known complement related diseases other than macular degeneration-related disorders. Complement related diseases or disorders have been described in the art, e.g., in U.S. Pat. No. 6,169,068. Examples of known complement related diseases include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, balloon angioplasty, post-pump syndrome in cardiopulmonary bypass or renal bypass, hemodialysis, renal ischemia, mesenteric artery reperfusion after acrotic reconstruction, infectious disease or sepsis, immune complex disorders and autoimmune diseases, rheumatoid arthritis, systemic lupus erythematosus (SLE), SLE nephritis, proliferative nephritis, hemolytic anemia, and myasthenia gravis. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gasses and chemicals, e.g., chlorine, phosgene, suffix dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, and immune complex-associated inflammation.

Genetic markers of risk of developing a macular degeneration-related disorder have been described above. The presence of any of these genetic markers in asymptomatic individuals signifies that a complement pathway-mediated process leading to a macular degeneration-related disorder is likely underway, although has not yet progressed so far as to produce symptoms.

A biochemical marker can be any of those described in the previous sections, such as an abnormal activity or abnormal level of, or an autoantibody against, a complement pathway molecule. If such a marker is detected, treatment should usually begin shortly thereafter. If likelihood of developing a macular degeneration-related disorder is based on relatives having the disease or detection of a genetic marker, treatment can also be administered shortly after identification of these risk factors, or shortly after diagnosis. Alternatively, an individual found to possess a genetic marker can be left untreated but subjected to regular monitoring for biochemical or symptomatic changes without treatment. The decision whether to treat immediately or to monitor symptoms depends in part on the extent of risk predicted by the various other marker(s) found in the subject. Once begun, the treatment is typically continued at intervals for a period of a week, a month, three months, six months or a year. In some subjects, treatment is administered for up to the rest of a subject's life. Treatment can generally be stopped if a biochemical risk marker disappears.

In addition to ocular diseases (e.g., AMD), subjects with other age-related diseases, such as amyloidosis, elastosis, dense deposit disease, and atherosclerosis, are also amendable to treatment with the methods of the present invention. Similarly, subjects with other types of macular degeneration-related disorders, e.g., membranous and post-streptococcal/segmental glomerulonephritis can also be treated with the presently claimed methods.

The second principal application of the methods lies in monitoring the condition of subjects receiving treatment for a macular degeneration-related disorder. A successful treatment outcome is indicated by return of complement pathway associated activity, such as expression level, biochemical activity (e.g., enzymatic activity of a complement component), or serum autoantibodies against complement pathway molecules, from abnormal levels to or toward normal levels. Typically, such methods measure an initial value for the level of abnormal activity (e.g., abnormal presence of an autoantibody, abnormal level of complement pathway molecule) before the subject has received treatment. Repeat measurements are then made over a period of time. If the initial level is elevated relative to the mean level in a control population, a significant reduction in level in subsequent measurements indicates a positive treatment outcome. Likewise, if the initial level of an measure marker is reduced relative to the mean in a control population, a significant increase in measured levels relative to the initial level signals a positive treatment outcome. Subsequently measured levels are considered to have changed significantly relative to initial levels if a subsequent measured level differs by more than one standard deviation from the mean of repeat measurements of the initial level. If monitoring reveals a positive treatment outcome, the same treatment regime can be continued, or replaced with a treatment regime with a lower dosage. If monitoring reveals a negative treatment outcome, the previous treatment regime is typically modified, either by using a different therapeutic agent or increasing the dosage of the previous agent.

In general, the subjects can be treated with a combination of different therapeutic agents of the present invention. The treatment can also proceed in conjunction with other known methods of treating macular degeneration-related disorders, e.g., antibiotic treatment as described in U.S. Pat. No. 6,218,368.

Further, immunosuppression could provide therapeutic effects in subjects suffering from, or at risk of developing, macular degeneration-related disorders (e.g., by inhibiting or ameliorating autoimmune responses). Thus, subjects to be treated with therapeutic agents of the present invention can also be administered with immunosuppressive agents such as cyclosporine. Immunosuppressive agents are agents capable of suppressing immune responses. These agents include cytotoxic drugs, corticosteriods, nonsteroidal antiinflammatory drugs (NSAIDs), specific T-lymphocyte immunosuppressants, and antibodies or fragments thereof (see Physicians' Desk Reference, 53rd edition, Medical Economics Company Inc., Montvale, N.J. (1999). Immunosuppressive treatment is typically continued at intervals for a period of a week, a month, three months, six months or a year. In some patients, treatment is administered for up to the rest of a patient's life. Treatment can generally be stopped if a biochemical risk marker disappears. Treatment can sometimes be temporarily discontinued if the subject is infected with a pathogen for which a full immune response is needed for clearance.

B. Modulation of Levels of Complement Pathway Molecules

The present invention provides methods for treating or preventing the development of macular degeneration-related disorders by modulating levels of complement pathway molecules. Levels of either mRNAs encoding the complement pathway associated proteins or levels of the complement pathway-associated proteins can be modulated. In some methods, the therapeutics are inhibitors of the expression of one or more complement components, e.g., complement 3, complement C5, or C5b-9 terminal complexes. In some methods, therapeutics are agents which alter the gene expression of factors that regulate the expression of one or more complement components. In some methods, therapeutics are agents which alter the gene expression of complement pathway molecules that regulate complement activity or activation, e.g., CR1, CR2, vitronectin, or clusterin.

Alteration of the above-noted gene expressions can be accomplished by a number of regimes, such as (i) modulation of mRNA synthesis, (ii) modulation of RNA turnover or degradation, (iii) modulation of translation of mRNA into protein, (iv) modulation of protein processing or transport, (v) modulation of formation of protein complex of the complement system (e.g., C3 convertase, C5 convertase, or the terminal complex C5b-9) by blocking inter- or intramolecular binding necessary for the formation; and (vi) modulation of the concentration of complement pathway molecules, e.g., by targeting and destroying complement components in situ (e.g., using enzyme-antibody techniques).

In some methods, the therapeutics of the invention relate to antisense therapy. By administration or in situ generation of oligonucleotide molecules which specifically hybridize to the cellular mRNA and/or genomic DNA encoding one or more complement pathway molecules, such a therapy functions by inhibiting expression of that protein, e.g., by inhibiting transcription and/or translation (see, e.g., Stanley et al., Basic Principles of Antisense Therapeutics, Springer-Verlag, NY, p. 3, July 1998). The binding can be by conventional base pair complementarity, or, for example, in the case of binding to DNA duplexes, through specific interactions in the major groove of the double helix.

In some methods, the therapeutic agents utilize zinc finger motif which can be selected to bind diverse nucleic acid sequences (see, e.g., U.S. Pat. No. 6,140,466). For example, therapeutic agents which activate or repress a target nucleic acid expression can be expressed as fusions with zinc finger motifs. Such fusion proteins are useful for inhibiting, activating or enhancing gene expression from a zinc finger-nucleotide binding motif containing promoter or other transcriptional control element, as well as a structural gene or RNA sequence.

C. Modulation of Complement Activity

The present invention provides methods of treatment or prevention of macular degeneration-related disorders by administering therapeutic agent which modulate bioactivities of the complement pathway molecules or cellular activities mediated by the activated complement system. In addition to methods described herein, methods for administering therapeutic agents to modulate complement activities in a subject have also been described in the art. For example, U.S. Pat. No. 5,472,939 describes modulation of complement mediated activities by administering to a subject CR1 or its fragment which inhibits C3 convertase activity or C5 convertase activity.

Various therapeutic agents are suitable for the present invention. Some agents are known in the art to be able to modulate the activities of complement components (see, e.g., U.S. Pat. No. 5,808,109). Many agents have been reported to diminish complement-mediated activity. Such agents include: amino acids (Takada, Y. et al. Immunology 1978, 34, 509); phosphonate esters (Becker, L. Biochem. Biophy. Acta 1967, 147, 289); polyanionic substances (Conrow, R. B. et al. J. Med. Chem. 1980, 23, 242); sulfonyl fluorides (Hansch, C.; Yoshimoto, M. J. Med. Chem. 1974, 17, 1160, and references cited therein); polynucleotides (DeClercq, P. F. et al. Biochem. Biophys. Res. Commun. 1975, 67, 255); pimaric acids (Glovsky, M. M. et al. J. Immunol. 1969, 102, 1); porphines (Lapidus, M. and Tomasco, J. Immunopharmacol. 1981, 3, 137); several anti-inflammatories (Burge, J. J. et al. J. Immunol. 1978, 120, 1625); phenols (Muller-Eberhard, H. J. 1978, in Molecular Basis of Biological Degradative Processes, Berlin, R. D. et al., eds. Academic Press, New York, p. 65); and benzamidines (Vogt, W. et al Immunology 1979, 36, 138). Some of these agents function by general inhibition of proteases and esterases. Others are not specific to any particular intermediate step in the complement pathway, but, rather, inhibit more than one step of complement activation. Examples of the latter compounds include the benzamidines, which block C1, C4 and C5 utilization (see, e.g., Vogt et al. Immunol. 1979, 36, 138).

Additional agents known in the art that can inhibit activity of complement components include K-76, a fungal metabolite from Stachybotrys (Corey et al., J. Amer. Chem. Soc. 104: 5551, 1982). Both K-76 and K-76 COOH have been shown to inhibit complement mainly at the C5 step (Hong et al., J. Immunol. 122: 2418, 1979; Miyazaki et al., Microbiol. Immunol. 24: 1091, 1980), and to prevent the generation of a chemotactic factor from normal human complement (Bumpers et al., Lab. Clinc. Med. 102: 421, 1983). At high concentrations of K-76 or K-76 COOH, some inhibition of the reactions of C2, C3, C6, C7, and C9 with their respective preceding intermediaries is exhibited. K-76 or K-76 COOH has also been reported to inhibit the C3b inactivator system of complement (Hong et al., J. Immunol. 127: 104-108, 1981). Other suitable agents for practicing methods of the present invention include griseofulvin (Weinberg, in Principles of Medicinal Chemistry, 2d Ed., Foye, W. O., ed., Lea & Febiger, Philadelphia, Pa., p. 813, 1981), isopannarin (Djura et al., Aust. J. Chem. 36: 1057, 1983), and metabolites of Siphonodictyon coralli-phagum (Sullivan et al., Tetrahedron 37: 979, 1981).

D. Macular Degeneration-related Autoantigens and Tolerance

As discussed in the Examples, infra, autoantibodies against various complement pathway molecules and against RPE, choroid, and retina proteins were found in serum of patients with macular degeneration-related disorders (e.g., AMD and Malattia Leventinese). This evidence indicates that autoimmune response play certain roles in the etiology macular degeneration-related disorders. Thus, identification of macular degeneration-associated autoantigens and/or autoantibodies also provides novel means for treating or preventing macular degeneration-related disorders. For example, novel therapeutics specifically directed to these autoantigens can be designed and produced, e.g., by computed-aided methods (see, e.g., Topper et al., Clin Orthop, -HD-(256):39-43, 1990).

The presence of macular degeneration-associated autoantigens and autoantibodies underscores how these molecules can activate the complement system and subsequent damages to the ocular tissues (e.g., choriocapillaris in RPE/choroid interface). For example, the complement system can be activated, e.g., by antigen-antibody complexes formed by the autoantigens and autoantibodies through the classic pathway. However, they can also activate the complement system through the other pathways, as demonstrated by the present inventors (see, e.g., Example 6). Thus, identification of the macular degeneration-related autoantigens provides another means of treating or preventing macular degeneration through induction in a subject of tolerance to the specific macular degeneration-related autoantigen. Induction of immunological tolerance is a therapeutic or preventive method in which a lack of immune responses to certain antigens is achieved. Induction of tolerance against a given antigen can be performed as described, e.g., in U.S. Pat. Nos. 6,153,203, 6,103,235, and 5,951,984.

To induce tolerance, it is to be noted that the nature of response (i.e., immunogenic or tolerogenic) depends on the dose, physical form and route of administration of antigen. High or low doses of an antigen often lead to immunotolerance, whereas intermediate doses may be immunogenic. Monomeric forms of antigen are usually tolerogenic, whereas high molecular weight aggregates are likely to be immunogenic. Oral, nasal, gastric or intravenous injection of antigen frequently leads to tolerance, whereas intradermal or intramuscular challenge especially in the presence of adjuvants favors an immunogenic response. See Marx, Science 252, 27-28 (1991); Trentham et al., Science 261, 1727-1730 (1993); Metzler & Wraith, International Immunology 5, 1159-1165 (1993); Cobbold et al., WO90/15152 (1990).

Identification of macular degeneration-related autoantigens also provide means for further understanding the genetic nature of macular degeneration-related disorders. Similar to many other diseases, mutations in the genes which encode the macular degeneration-associated autoantigens (e.g., complement pathway associated proteins, or the RPE autoantigens) can be the genetic cause of macular degeneration-related disorders. For example, a number of diseases are due to deficiencies in proteins associated with the complement pathway, and the deficiency is often due to mutations in the complement protein. Examples of such disease include: SLE like symptoms (point mutation in C1q); hereditary angioedema (mutations and polymorphisms in C1q inhibitor); SLE (deletions in C2); pyogenic infections (61bp deletion in exon 18 of C3 gene); membranoproliferative (C3); glomerulonephritis (C3); partial lipodystrophy (C3); SLE (frameshift in C4a); predisposition to Neisseria (C6: stop codon insertion leading to truncated gene product); meningitis and Neisseria infection (Factor P (Properdin): point mutations; X-linked); autosomal recessive atypical hemolytic uremic syndrome (Factor H: point mutations); aplastic anemia and paroxysmal nocturnal hemoglobinuria (PNH (CD59: deletion in codon 16, also single base pair mutations; and PNH (CD55, deletion point mutation).

To identify the genetic causes of macular degeneration-related disorders, the specific autoantigens identified, e.g., as described in Examples 9-13, can be subject to further analysis. For example, the identity and sequence information of the autoantigens can be revealed by standard amino acid sequencing procedures (e.g., Current Protocols in Molecular Biology, Ausubel, F. M. et al., 1999, John Wiley & Sons, Inc., New York) as well as other methods for protein identification (e.g., matrix assisted-laser desorption ionization mass spectrometry, as disclosed in Example 11). Polynucleotide primers can be generated and used to clone the genes which encode these autoantigens with standard techniques routinely practiced in molecular biology (Sambrook et al., Molecular Cloning A Laboratory Manual, 3rd Ed, 2000, Cold Spring Harbor Laboratory Press). The nucleotide sequences of such autoantigens can thus be obtained. The sequences can be compared with the DNA sequences from the genomic databases (e.g., GenBank). Any mutation or polymorphism identified in the autoantigen-encoding sequence relative to a wild type sequence would indicate that the corresponding gene is a likely candidate which causes the macular degeneration-related disorder.

E. Screening for Novel Therapeutics for Macular Degeneration-related Disorders

1. Test Agents

The present invention provides methods for prevention or treatment of diseases or disorders associated with abnormal complement activity by administering therapeutic agents that modulate complement activity. In addition to the above-described agents, therapeutic agents that modulate complement activity can also be obtained by screening test agents with high throughput screening techniques.

Test agents that can be screened with include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Usually, test compounds are organic. Some test compounds are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal exacts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be filly randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

Libraries of test agents to be screened can also be generated based on structural studies of a target complement pathway molecule. Such structural studies allow the identification of test agents that are more likely to bind to the target molecule. The three-dimensional stricture of a complement pathway molecules can be studied in a number of ways, e.g., crystal structure and molecular modeling. Methods of studying protein structures using x-ray crystallography are well known in the literature. See Physical Bio-chemistry, Van Holde, K. E. (Prentice-Hall New Jersey 1971), pp. 221-239, and Physical Chemistry with Applications to the Life Sciences, D. Eisenberg & D. C. Crothers (Benjamin Cummings, Menlo Park 1979). Computer modeling of the structures of complement pathway molecules provides another means for designing test compounds for screening modulators of complement system. Methods of molecular modeling have been described in the literature, e.g., U.S. Pat. No. 5,612,894 entitled "System and method for molecular modeling utilizing a sensitivity factor", and U.S. Pat. No. 5,583,973 entitled "molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interscience, New York 1986).

Therapeutic agents of the present invention also include antibodies that specifically bind to the various complement pathway molecules (e.g., C5b). Such antibodies can be monoclonal or polyclonal, and many are described in the art. In addition, methods for producing antibodies are well known in the art. For example, the production of non-human monoclonal antibodies, e.g., murine or rat, can be accomplished by, for example, immunizing the animal with a given complement component protein or an antigenic fragment thereof (See Harlow & Lane, Antibodies, A Laboratory Manual, Cold Spring Harbor Laboratory Press, Cold Spring Harbor N.Y.). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to the complement protein or antigenic fragment.

Human antibodies against a complement pathway molecule can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991).

Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using the complement component or an antigenic fragment as an affinity reagent.

2. Cell-free Assays for Detecting Binding Between a Test Agent and a Complement Pathway Molecule Cell-free assays can be used to identity agents which are capable of interacting with a complement pathway molecule and modulating its activity and/or interaction with another molecule. Binding of a test agent to a complement pathway molecule is determined in a reaction mixture. Binding can be assayed by a number of methods including, e.g., labeled in vitro protein-protein binding assays, electrophoretic mobility shift assays, immunoassays for protein binding, functional assays (e.g., phosphorylation assays, etc.). See, e.g., U.S. Pat. Nos. 4,366,241; 4,376,110; 4,517,288; and 4,837,168, and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to the complement component, e.g., co-immunoprecipitation of with the complement component. The test agent can also be identified by detecting a signal that indicates that the agent binds to the complement component, e.g., fluorescence quenching.

Competition assays provide a suitable format for identifying test compounds that specifically bind to a complement pathway molecule. In such formats, test compounds are screened in competition with a compound already known to bind to the complement pathway molecule. The known complement-binding agent can be a synthetic polypeptide. It can also be an antibody which specifically recognizes the complement pathway molecule. If the test compound inhibits binding of the compound known to bind the complement pathway molecule, then the test compound also binds the complement pathway molecule.

Numerous types of competitive binding assays are known, e.g., solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137: 3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Mol. Immunol. 25(1):7-15 (1988)); solid phase direct biotin-avidin EIA (Cheung et al., Virology 176:546-552 (1990)); and direct labeled RIA Moldenhauer et al., Scand. J. Immunol. 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

The screening assays can be either in insoluble or soluble formats. One example of the insoluble assays is to immobilize a given complement pathway molecule, or a fragment thereof, onto a solid phase matrix. The solid phase matrix is then put in contact with test agents for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing the complement pathway molecule, the test agents are bound to the solid matrix and the complement pathway molecule is then added.

Soluble assays include some of the combinatory libraries screening methods and the genetic screening systems described above. Under the soluble assay formats, neither the test agents nor the complement pathway molecule are bound to a solid support. Binding of a complement pathway molecule or fragment thereof to a test agent can be determined by, e.g., changes in fluorescence of either the complement pathway molecule or the test agents, or both. Fluorescence may be intrinsic or conferred by labeling either component with a fluorophor. Binding can be detected by fluorescence polarization.

In some binding assays, either the complement pathway molecule, the test agent, or a third molecule (e.g., an anti-complement antibody) as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}$I, $^{32}$P, $^{35}$S) or a chemiluminescent or fluorescent group. Similarly, the detectable group can be a substrate, cofactor, inhibitor or affinity ligand.

Some test compounds with specific binding activity to a given complement pathway molecule (e.g., C5b) identified by such assays are specific to that complement pathway molecule and can be used to modify the activity of only that complement pathway molecule. Other test compounds show specific binding to a plurality of complement pathway molecules and can be used to modulate the activity of all of these complement pathway molecule.

3. Cell-based Assays

An interaction between the test compound and the complement pathway molecule or between the complement pathway molecule and the complement pathway molecule binding partner can also be detected with cell-based assays. For example, a microphysiometer described in McConnell et al. (1992) Science 257:1906 can be used. Cell based assays can also be used to identify compounds which modulate expression of a gene encoding a complement pathway molecule, modulate translation of a mRNA encoding a complement component, or which modulate the stability of the complement pathway protein or its mRNA.

In some methods, to identify an reagent which modulate expression of a complement pathway molecule, a cell which is capable of expressing a complement pathway molecule is incubated with a test compound and the amount of complement pathway molecule produced in the cell medium is measured and compared to that produced from a cell which has not been contacted with the test compound. Compounds which can be tested include small molecules, proteins, and nucleic acids. In particular, this assay can be used to determine the efficacy of antisense or ribozymes to genes encoding a complement component.

In other methods, the effect of a test compound on transcription of a gene encoding a complement pathway molecule is determined by transfection experiments using a reporter gene operatively linked to at least a portion of the promoter of a gene encoding a complement pathway molecule. A promoter region of a gene can be isolated, e.g., from a genomic library according to methods known in the art. The reporter gene can be any gene encoding a protein which is readily quantifiable, e.g., the luciferase or CAT gene. Such reporter gene are well known in the art.

F. Formulation and Dosages

1. Formulations and Modes of Administration

Therapeutics of the present invention can be formulated in a conventional manner using one or more physiologically acceptable carriers or excipients. Thus, the therapeutic agents described above can be formulated for administration by, for example, eye drops, injection, inhalation or insufflation (either through the mouth or the nose) or oral, buccal, parenteral or rectal administration. Treatment can also follow guidance provided in the art. For example, pulmonary administration of soluble complement receptor-1 (sCR1) to treat certin medical conditions (U.S. Pat. No. 6,169,068), intraocular administration of drugs to treat macular degeneration (U.S. Pat. No. 5,632,984), and treatment of macular edema with topical administration of carbonic anhydrase inhibitors to the eye (U.S. Pat. No. 6,046,223) have all been described in the art.

The therapeutic agents of the invention can be formulated for a variety of modes of administration, including systemic and topical or localized administration. Techniques and formulations generally can be found in Remmington's Pharmaceutical Sciences, Meade Publishing Co., Easton, Pa. The compositions are formulated as sterile, substantially isotonic and in full compliance with all Good Manufacturing Practice (GMP) regulations of the U.S. Food and Drug Administration. A preferred method of administration is an eye drop. For systemic administration, injection is preferred, including intramuscular, intravenous, intraperitoneal, and subcutaneous.

Preferred methods of administration include, e.g., choroidal injection, transscleral injection or placing a scleral patch, selective arterial catheterization, intraocular administration including transretinal, subconjunctival bulbar, scleral pocket and scleral cutdown injection. The agent can also be alternatively administered intravascularly, such as intravenously (IV) or intraarterially. In choroidal injection and scleral patching, the clinician uses a local approach to the eye after initiation of appropriate anesthesia, including painkillers and ophthalmoplegics. A needle containing the therapeutic compound is directed into the subject's choroid or sclera and inserted under sterile conditions. When the needle is properly positioned the compound is injected into either or both of the choroid or sclera. When using either of these methods, the clinician can choose a sustained release or longer acting formulation. Thus, the procedure can be repeated only every several months or several years, depending on the subject's tolerance of the treatment and response.

For injection, the compounds of the invention can be formulated in liquid solutions, preferably in physiologically compatible buffers such as Hank's solution or Ringer's solution. In addition, the compounds can be formulated in solid form and redissolved or suspended immediately prior to use. Lyophilized forms are also included.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The therapeutic can be administered alone or in combination with other molecules known to have a beneficial effect on retinal attachment or damaged retinal tissue, including molecules capable of tissue repair and regeneration and/or inhibiting inflammation. Examples of useful cofactors include basic fibroblast growth factor (bFGF), LaVail et al. (1998), Invest. Ophthalmol. Vis. Sci. 39:592-602, ciliary neurotrophic factor (CNTF), LaVail et al. (1998), Invest. Ophthalmol. Vis. Sci. 39:592-602, axokine (a mutein of CNTF), LaVail et al. (1998), Invest. Ophthalmol. Vis. Sci. 39:592-602, leukemia inhibitory factor (LIF), LaVail et al. (1998), Invest. Ophthalmol. Vis. Sci. 39:592-602. neutrotrophin 3 (NT-3), LaVail et al. (1998), Invest. Ophthalmol. Vis. Sci. 39:592-602, neurotrophin-4 (NT-4), LaVail et al. (1998), Invest. Ophthalmol. Vis. Sci. 39:592-602, nerve growth factor (NGF), LaVail et al. (1998), Invest. Ophthalmol. Vis. Sci. 39:592-602, insulin-like growth factor II, LaVail et al. (1998), Invest. Ophthalmol. Vis. Sci. 39:592-602, prostaglandin E2, La Vail et al. (1998), Invest. Ophthalmol. Vis. Sci. 39:581-591, 30 kD survival factor, taurine, and vitamin A. Other useful cofactors include symptom-alleviating cofactors, including antiseptics, antibiotics, antiviral and antifungal agents and analgesics and anesthetics.

A therapeutic also can be associated with means for targeting the therapeutics to a desired tissue. For example, in some methods, a therapeutic agent can be directed to the choriocapillaris which is implicated to be a target of activated complement system (e.g., C5-9 complex) in AMD patients. Useful targeting molecules can be designed, for example, using the simple chain binding site technology disclosed, e.g., in U.S. Pat. No. 5,091,513. Thus, by targeted delivery, therapeutic agents are aimed to prevention or alleviation of damages to the choriocapillaris caused by the C5b-9 complex. Such effects can be achieved by the various means described above, e.g., inhibiting complement activation, stimulating the functions of the complement pathway inhibitors (e.g., clusterin, vitronectin), or disrupting the complex already form on the choriocapillaris.

In clinical settings, a gene delivery system for a gene therapeutic can be introduced into a subject by any of a number of methods. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), *Proc. Natl. Acad. Sci., USA* 91: 3054-3057. A sequence homologous thereto can be delivered in a gene therapy construct by electroporation using techniques described, Dev et al. (1994), *Cancer Treat. Rev.* 20:105-115.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

2. Dosages

Toxicity and therapeutic efficacy of such compounds can be determined by standard pharmaceutical procedures in cell cultures or experimental animals, e.g., for determining the $Ld_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. Molecular Cloning A Laboratory Manual (1989), $2^{nd}$ Ed., ed. by Sambrook, Fritsch and Maniatis, eds., *Cold Spring Harbor Laboratory Press*, Chapters 16 and 17; Hogan et al. (Manipulating the Mouse Embryo: A Laboratory Manual (1986), *Cold Spring Harbor Laboratory Press*, Cold Spring Harbor, N.Y.; See U.S. Pat. No. 4,683,195; *DNA Cloning*, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, *Alan R Liss, Inc.*, 1987; Immobilized Cells And Enzymes, IRL Press, 1986; Perbal (1984), A Practical Guide To Molecular Cloning; See Methods In Enzymology (*Academic Press, Inc.*, N.Y.); Gene Transfer Vectors For Mammalian Cells, J. H. Miller and M. P. Calos, eds., *Cold Spring Harbor Laboratory*, 1987; Methods In Enzymology, Vols. 154 and 155, Wu et al., eds., *Academic Press Inc.*, N.Y.; Immunochemical Methods In Cell And Molecular Biology (Mayer and Walker, eds., *Academic Press*, London, 1987; Handbook Of Experimental Immunology, Volumes I-IV, D. M. Weir and C. C. Blackwell, eds., 1986.

Many modifications and variations of this invention can be made without departing from its spirit and scope. The specific examples described herein are for illustration only and are not intended to limit the invention in any way.

All publications, figures, patents and patent applications cited herein are hereby expressly incorporated by reference for all purposes to the same extent as if each was so individually denoted.

EXAMPLES

Example 1

Identification of Complement Pathway Molecules in Drusen, Bruch's Membrane, and Choriocapillaris Tissues: Eyes from the human donor repository and CDD, ranging in age between 45 and 101 years, were processed within four hours of death Many of these donors had a documented clinical diagnosis of AMD (including donors with geographic atrophy, choroidal neovascularization, and disciform scars in at least one eye) and one donor was diagnosed with cuticular drusen. Human liver was obtained within 2 hours of biopsy. RPE cells were isolated with 2% dispase within 5 hours of death and were grown in Coon's F-12 media with 10% fetal bovine serum.

Immunohistochemistry:

Tissues were fixed for at least two hours in one-half strength Karnovsky fixative (½K; 2% formaldehyde and 2.5% glutaraldehyde in 100 mM cacodylate buffer, pH 7.4, containing 0.025% CaC12) prior to washing 3×10 min. in 100 mM cacodylate buffer. Slides were blocked for 15 min. in 0.01M sodium phosphate (pH 7.4) containing 0.85% NaCl, 1 mM calcium chloride, 1 mM magnesium chloride (PBS/M/C), and 1 mg/ml globulin-free bovine serum albumin (PBS/M(C/BSA). Sections were then rinsed for 10 min. in PBS/M(C, incubated in primary antibody diluted in PBS/M/C/BSA, for one hr., at room temperature. In some cases, sections were pretreated, prior to blocking, with 0.5% trypsin (Sigma, St. Louis, Mo.) for 10 min. as specified by the supplier. Following exposure to primary antibody, sections were rinsed (2×10 min.) in PBS/M/C, incubated in the appropriate fluorescein-conjugated-secondary antibody (often adsorbed against human serum) diluted in PBS/M/C/BSA (30 min., room temperature), rinsed (2×10 min) in PBS/M/C, and mounted in Immumount (Shandon, Pittsburgh, Pa.). Adjacent sections were reacted with secondary antibody alone, as negative controls. Some sections were pre-treated for 10 min with 0.5% trypsin (Sigma; St. Louis, Mo.), or 0.2-0.02 U/ml chondroitinase ABC (Seikagaku; Rockville, Md.), for use in conjunction with antibodies for collagen type IV or various chondroitin sulfate proteoglycans, respectively. Drusen-containing tissues from a minimum of five donor eyes were examined for each antibody.

For negative controls, sections were exposed to PBS/M/C/BSA containing: a) no primary antibody; b) 1% (v/v) normal serum; and/or c) antibodies to irrelevant proteins. In some cases, an additional control included adsorption of primary antibody to purified antigen. Positive controls included reaction of antibodies with the extracellular matrices of sclera, choroid, and vitreous; retinal and choroidal basal laminae; retinal interphotoreceptor matrix; and liver. In order to determine the "specificity" of serum protein accumulation in drusen, drusen-containing sections were reacted with antibodies to human albumin (Cappel; Malvern, Pa.) and haptoglobin (Dako; Carpenteria, Calif.). Haptoblobin is a macromolecular glycoprotein which is the major acute phase reactant (Putnam, *Haptoglobin*, In: *The Plasma Proteins, Structure, Function, and Genetic Control*, 11, Putnam (ed.), Academic Press, New York, pp. 1-50, 1975; and Morimatsu et al., J. Biol. Chem., 266:11833-11837, 1991).

Results

Reactivities of antibodies with drusen are listed in Table 1 below. In general, all positive antibodies bound to all drusen phenotypes. Controls confirm all antibody reactivities to be specific. In addition, the majority of the antibodies utilized bound to the expected regions of sclera, choroid, RPE, retina, vitreous, and/or other "control" tissues.

TABLE 1

Drusen associated molecules (DRAMs)

| ANTIGEN | SOURCE | DRUSEN |
|---|---|---|
| α1 antichymotrypsin | Dako | + |
| α1 antitrypsin | Dako | −/+ |
| α2 macroglobin | Biodesign | − |
| aFGF | | − |
| AKS | | − |
| Albumin | Cappel | − |
| Amyloid A | Dako | + |
| Amyloid b | Dako | − to +/− |
| Amyloid P | Dako | + |
| Amyloid Prec Prot | B-M | − |
| Antithrombin-III | Calb | +/− |
| Apo A1 | Calb | − |
| Apo E | Calb | + |
| ASPG-1 | | − |
| Atrial Natriuretic Factor | Chemicon | − |
| β2 microglobin | B-M | +/− |
| bFGF | | − |
| Basement Membrane | Chemicon | − |
| Bovine nas. cart. p. | ICN | − |
| CD1a | Dako | + |
| CD3 | Pharm | −/+ |
| | Dako | − |
| CD4 | Pharm | +/− |
| CD8 | Pharm | − |
| CD14 | Dako | + |
| CD15 | Chemicon | − |
| CD31 | Dako | +/− |
| CD44 | Various | − |
| CD45 | Dako | + |
| CD68 | Dako | + |
| CD83 | | + |
| CD86 | Dako | + |
| CRP | Dako | − to +/− |
| Calcitonin | Dako | − |
| Carbonic Anhydrase | | − |
| Carc Assoc Ag | | − |
| cfms/CSF-1 receptor | | − |
| Chondroitin sulfate | | − |
| Chondroitin 0 sulfate | | − |
| Chondroitin 4 sulfate | | + |
| Chondroitin 6 sulfate | | + |
| Chondroitin sulfate PG | Chemicon | − |
| Collagen I | Southern Biotech | − |
| Collagen II | SB | − |
| Collagen III | SB | − |
| Collagen IV | SB, Chemicon | − |
| Collagen V | SB | − |
| Collagen VI | | − |
| Collagen VII | | − |
| Collagen IX | | − |
| Collagenases | | |
| C1q | Calb | −/+ |
| Complement 3 | | − to + |
| C5 | | + |
| C5-C9 complex | Calb | +/− |
| COS | | − |
| CRALBP | | − |
| Cystatin C | | − |
| Decorin | Chemicon | − |
| Elastin | Sigma | − |
| Entactin | | − |
| Factor X | Dako | + |
| Fibrin | | − |
| Fibrinogen | Dako | − to +/− |
| Fibronectin | | − |
| Fibulin 3 | Timpl | −/? |
| Fibulin 4 | Timpl | −/? |
| FnR | | − |
| α Fodrin | | − |
| β Fodrin | | −/+ |
| Gangliosides | Dev Hyb | − |
| Gelsolin | | − |
| GFAP | | − |
| Glucose Transporters 1, 3, 4 | | − |
| Glycolipid | Dev Hyb | − |
| Glycophorin A, C | | − |
| Haptoglobin | Dako | +/− (variable) |
| Heckenlively serum Ag | | +/− |
| Heparan sulfate | (MAB) | +/− |
| (MAC) | | |
| Kimata | | |
| Hermes | | − |
| HLA ABC | | −/? |
| HLA DR | Various | + |
| HNK-1 | | − |
| Heat Shock Prot 70 | | − |

TABLE 1-continued

Drusen associated molecules (DRAMs)

| ANTIGEN | SOURCE | DRUSEN |
|---|---|---|
| HSPG | | – |
| Human IgA | | – |
| Human IgG | | +/– |
| Hyaluronic Acid | | – |
| Ig Kappa chain | | – to +/– |
| Ig Lambda chain | Dako | +/– to + |
| Integrin α2 | | – |
| Integrin α3 | | – |
| Integrin α4 | | – |
| Integrin α5 | | – |
| Integrin α6 | | – |
| Integrin β1 | | – |
| Integrin β2 | | – |
| Integrin β4 | | – |
| Intermediate Filaments | | – |
| Interphotoreceptor Matrix | | – |
| IRBP | | – |
| Keratan sulfate | | – |
| Keratin | | – |
| Laminin | | – |
| LAMP-1 | Dev Hyb | – |
| LAMP-2 | Dev Hyb | – |
| Link Protein | Dev Hyb | – |
| Lipoprotein b | | – to +/– |
| Melanoma Assoc Ag | | – |
| Milk mucin core Ag | | – |
| MMPs | | – |
| Mitochindrial Ag | | – |
| N.S. Enolase | | – |
| Nerve Growth Factor | | – |
| NGFR | | – |
| Neurofibrillary tangles | | – |
| PG40 (Decorin) | | – |
| Phospholipase A2 | | – |
| Plasminogen# | Dako | + |
| Plasminogen Act. Inhib.-1 | | – |
| Platelet Derived GF | | – |
| Prealbumin# | B-M | – to + |
| Prothrombin# | | +/– |
| S-100 (Bovine) | | –/? |
| Sialo Cell Surface Ag | | – |
| Tau | | – |
| Tenascin | | – |
| TGFb | | – |
| Thrombin | Sera | +/– |
| Thrombospondin | (Gib/AMAC) | – to +/– |
| TIMP1 | | – |
| TIMP2 | | – |
| TIMP3 | | + |
| TIMP4 | | +/– |
| Tubulin | | – |
| Ubiquitin | | – to + |
| UPAR | Anderson | – |
| Vimentin | | – |
| Vitronectin | Various | + |
| VnR | | – |
| von W Factor | | – |

B-M = Boehringer-Mannheim;
Calb = Calbiochem;
Gib = Gibco/BRL;
Pharm = Pharmingen;
Sera = Sera Labs;
Tel = Telios;
"–" no reactivity;
"+" consistent positive reactivity;
"+/–" weak reactivity;
"–/+" very weak reactivity Example 2

Identification of Complement Pathway Components, Including the Activated C5b-9 Membrane Attack Complex, in Drusen and Bruch's Membrane As demonstrated in Example 1, proteins associated with cellular and humoral immune processes, including amyloid A component, amyloid P component, apolipoprotein E, factor X, MHC class II molecules, vitronectin, and complement proteins (C3, C5 and C5b-9 complex) are prevalent among the drusen-associated constituents identified. Other complement components, including the terminal complement complex C5b-9 (the membrane attack complex, MAC), are also distributed within Bruch's membrane at the RPE-choroid interface. The presence of widespread terminal C5b-9 complement complexes within Bruch's membrane and drusen indicates that inappropriate complement activation can occur within the sub-RPE space. The abnormal process can have injurious effects on the RPE and/or choroidal cells, promote neovascularization and microangiopathy (including loss of pericytes and hyperplasia of endothelial cells), increase blood vessels permeability and/or promote recruitment of monocytes, thereby contributing to the pathology of AMD.

Studies were conducted to examine complement pathway molecules in eyes derived from donors with and without AMD using immunohistochemical, ELISA, and Western blot analyses. These studies were aimed to identification of complement pathway-associated constituents that are present at the RPE-choroid interface, to identify the specific complement pathway(s) that is activated, to determine whether the C5b-9 complex is inserted into the membranes of local ocular cells, to determine whether complement components are synthesized by locally by ocular cells, and to assess the relative amounts of mRNAs coding for complement constituents in eyes from donors with and without AMD.

Numerous complement pathway proteins were found to be associated with drusen, Bruch's membrane, the basal surface of the RPE, and/or the sub-RPE space using immunohistochemistry (Table 2). Complement pathway-associated molecules localized to the basal surface of the RPE include CD21, CD35, CD55/decay accelerating factor, and CD59/protectin. Complement pathway-associated molecules localized in Bruch's membrane and/or drusen include C3d, C6, C7, C8, C9, Factor D, Factor H, Factor I, Factor B, SP40,40 (clusterin), and mannose binding protein, in addition to the previously described complement components C3, C5 and the terminal complement complex C5b-9. Complement pathway components C1q, C1 inhibitor, C2, C3a, C4, C5a, and Factor Ba are present within the choroidal stroma, but do not appear to be major components of drusen or Bruch's membrane. The presence of many of these complement pathway-associated components has been confirmed using ELISA and Western analyses (Table 2).

TABLE 2

Identification of Complement Pathway-Associated Molecules Within the Human RPE-Choroid

| | Western (RPE/Ch) | Western (RPE) | ELISA (RPE/Ch) | ELISA (RPE) | Immunohistochemistry (Donor Numbers) |
|---|---|---|---|---|---|
| Ig κ | ND | ND | ND | ND | CH+, D+/− (459-00) |
| Ig γ | +(205-98) | +(205-98) | +(411-99) | +(411-99) | CH+, D− (33-99, 459-99) |
| C1q | ND | −(411-99) | −(325-00, 294-00) | +(411-99, 205-98) | CH+/−, D−, RPE+, (239-00, 58-00, 407-99, 247-99, 86-98, 294-00, 242-00) |
| C1 inhibitor | ND | +(86-98, 247-99) | +(325-00, 294-00) | +/− (242-00) | RPE+, D+/− (242-00) |
| C2 | +(294-00) | +(294-00) | ND | ND | CH+. D−/+ (294-00) |
| C4 | +(294-00) | +(294-00) | ND | ND | CH+, D−/+ (294-00) |
| C3 | ND | −(247-99, 86-98) | ND | ND | CH+, D− (239-00, 58-00, 407-99, 247-99, 459-99, 294-99, 97-99) |
| C3a | ND | +/−(86-98, 247-99) | ND | +(205-98) | CH+, D− (1-97, 459-00, 239-00, 242-00) |
| C3d | +(294-00, 325-00) | ND | +(325-00, 294-00) | ND | CH+, D+, RPE+, cores? (294-00, 94-00, 404-00, 453-00, 325-00) |
| C5 | ND | +/−(205-98, 411-99) | +(325-00, 294-00) | +(325-00, 294-00) | CH+/−, D+ (242-00, 239-00, 407-99, 247-00) |
| C5a | ND | +/−(86-98, 247-99) | +(325-00, 294-00) | +(205-98) | CH+, D− (407-99, 247-99, 86-98, 242-00, 294-00) |
| C5b-9 | ND | −(86-98, 247-99) | +(325-00, 294-00) | +(205-98) | CH−/+, D+ (all 20 donors) |
| Clusterin | ND | +(242-00) | −(325-00, 294-00) | +(205-98) | D+ (242-00) |
| CD21 | ND | − | ND | ND | RPE+/− (239-00, 459-00, 294-00, 242-00, 58-00) |
| CD35 | ND | −(86-98, 247-99) | ND | −(242-00) | RPE+/− (58-00, 294-00, 239-00, 1-97, 459-99, 242-00) |
| CD55 | ND | −(242-00) | −(325-00, 294-00) | −(242-00) | RPE+ (239-00, 459-99) |
| CD59 | ND | −(242-00) | −(325-00, 294-00) | −(242-00) | RPE+, CH+ (242-00, 1-97, 459-99, 294-00) |
| Factor B | +/−(294-00, 242-00) | +(242-00, 294-00) | −/+(325-00, 294-00) | −(242-00) | CH+, D+/−, cores? (294-00) |
| Factor Ba | +(325-00, 294-00) | ND | −(325-00, 294-00) | −(242-00) | CH+, D− (294-00, 94-00, 404-00, 453-00, 325-00, 330-00, 457-00) |
| Factor D | ND | ND | ND | ND | DR+/− |
| Factor H | ND | −(325-00, 294-00) | +/−(325-00, 294-00) | +(205-98, 242-00) | CH−/+, D+ (242-00, 294-00, 459-00, 457-00, 330-00, 325-00, 94-00, 404-00, 453-00) |
| Factor I | +/−(294-00) | ND | +(325-00, 294-00) | ND | DR−/+, CH−/+ (294-00, 94-00, 404-00, 453-00, 325-00, 330-00) |
| Mannose Binding Protein | +/−(325-00, 294-00) | +/−(325-00, 294-00) | +/−325-00, 294-00) | +(242-00) | DR+, CH+ (294-00, 330-00, 457-00, 325-00, 94-00, 404-00, 453-00) |
| Mannose Receptor | −(325-00, 294-00) | −(325-00, 294-00) | ND | ND | −(294-00) |

Retinal pigmented epithelium (RPE) and RPE-choroid complexes (RPF/Ch) from 20 donors (five with a diagnosis of AMD and two with probable AMI) were used for various Western blot, ELISA and immunohistochemical studies of complement activation pathways. Donor designations are listed in parentheses in the table and the age, sex (M, male or F, female), race (C, Caucasian), and disease state (AMD) of each donor are detailed below.
450-99 30 CF
453-00 61 CM
411-99 67 CF Family history of AMD
247-99 70 CF
86-98 73 CM
407-99 74 CF AMD and family history of AMD
58-00 74 CM
330-00 75 CF Macular RPE changes (AMD?)
325-00 77 CF
404-00 77 CF Macular drusen (AMD?)
247-99 79 CF
94-00 80 CM
239-00 80 CF AMD and family history of AMD
459-00 80 CM
294-00 84 CF AMD

TABLE 2-continued

Identification of Complement Pathway-Associated Molecules
Within the Human RPE-Choroid

| Western (RPE/Ch) | Western (RPE) | ELISA (RPE/Ch) | ELISA (RPE) | Immunohistochemistry (Donor Numbers) |
|---|---|---|---|---|
| | | | | 33-99 86 CF AMD |
| | | | | 457-00 89 CF AMD |
| | | | | 205-98 91 CM |
| | | | | 242-00 99 CF |

"D" denotes drusen in the Table;
"+" positive labeling according to the assay;
"−" no labeling;
"+/−" weak labeling;
"−/+" very weak labeling

Example 3

Determination of the Relationship Between Terminal Complement Complex Deposition in Bruch's Membrane, Age, and AMD Based on the observation that the full spectrum of complement proteins and inhibitors, as well as activated complement complexes, are present at the RPE-choroid interface, the distribution of the C5b-9 terminal complement complex was examined in 30 human donor eyes ranging in age between less than 1 year and 94 years of age. The donors above the age of 60 were evenly divided between donors with and without AMD. In summary, a strong correlation between intensity and distribution of C5b-9 associated with the choriocapillaris and a diagnosis of AMD was observed.

Aldehyde-fixed sagittal wedges were infiltrated and embedded in acrylamide and optimal cutting temperature compound. Frozen sections were prepared and were labeled with two different monoclonal antibodies directed against the C5b-9 terminal complement complex neoantigen.

Figure 2:
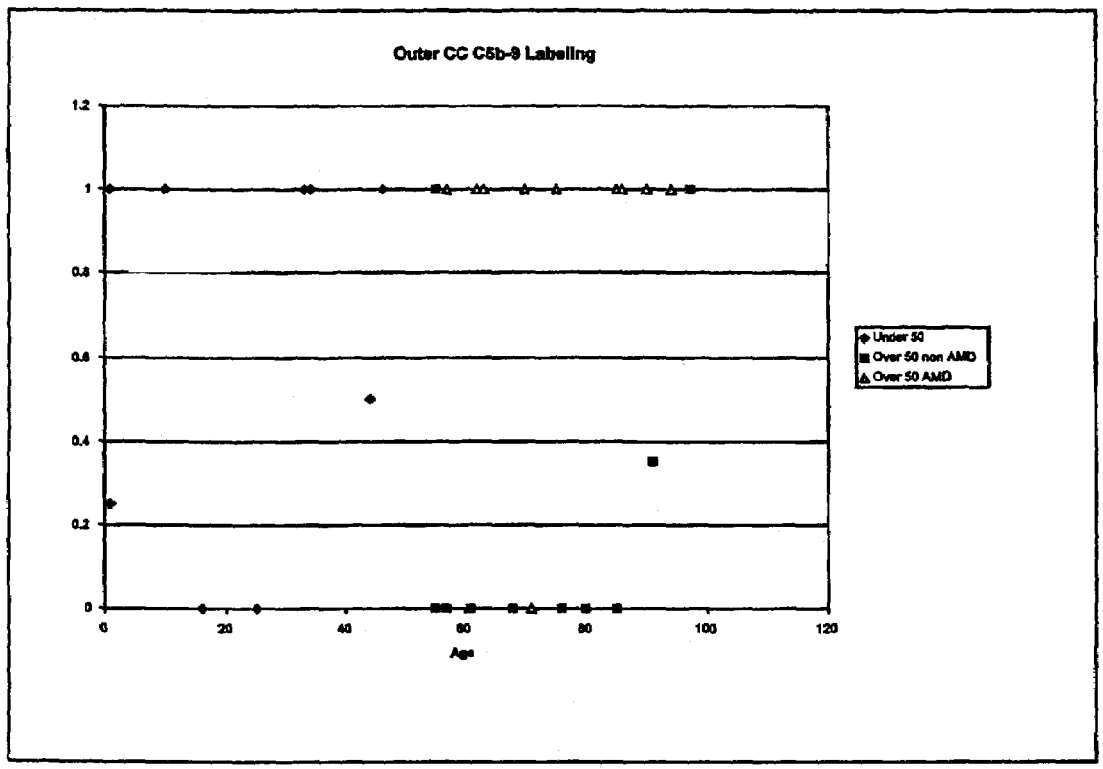
FIG. 2 shows distribution and intensity of C5b-9 in the RPE-choroid of human donor eyes.

Notably, Bruch's membrane also reacted with these antibodies in most of the donors evaluated. In younger donors, C5b-9 was observed in the outer collagenous layer of Bruch's membrane, with relatively little labeling of the inner collagenous layer. Sporadic labeling to the basal and lateral aspects of the choriocapillaris was also observed in some younger donors. The distribution of C5b-9 within Bruch's membrane "shifted" toward the inner collagenous layer in individuals of advanced age. In these individuals, C5b-9 was observed on both sides of the elastic lamina or, in some cases, solely within the inner collagenous layer. In addition, the antibodies directed against C5b-9 bound intensely to all drusen phenotypes in older individuals, as we have described previously (Mullins et al. FASEB J. 2000). Significantly, intense labeling of the entire choriocapillaris (endothelium, pericytes, and associated extracellular matrix) was observed in donors with AMD (9 of 10 donors), as compared to older, age-matched donors without a diagnosis of AMD (2 of 10 donors) (FIG. 2).

When combined with the observation that C5b-9 complexes are associated (most likely inserted into) with RPE and choroidal cell membranes (see above), these data imply that the choriocapillaris of AMD subjects may be under more rigorous attack than that of individuals without AMD. This may be due to an inability of local cells in individuals with AMD to inhibit and/or defend themselves against complement activation. The distribution of immunoreactive C5b-9 and detectable levels of C5b-9 in the samples from AMD donors implies that complement pathway inhibitors such as clusterin, vitronectin CD56 and CD55 may fail to suppress the terminal pathway, thereby permitting formation of MAC. Complement-mediated damage to the choriocapillaris, whether by direct insertion or due to bystander effects, may lead to abnormal responses by the choroid (e.g., inflammation, cytokine secretion, neovascularization) and/or choriocapillaris cell death. These events, in turn, may lead to further dysfunction and death of surrounding cells, including the RPE, and the biogenesis of drusen. Although this represents a paradigm shift in our thinking about the etiology of AMD, similar processes are indeed active in other diseases, including atherosclerosis and Alzheimer disease. These data also provide evidence that Bruch's membrane may serve as an unusual activating surface for complement in its physiologically "normal" state, and/or that activated C5b-9 is poorly cleared from Bruch's membrane compared with other structures in the healthy choroid. Whatever the precise pathways and initiating events that are involved, it is clear that complement activation occurs at the RPE-choroid interface chronically and that a strong correlation between intensity and distribution of C5b-9 associated with the choriocapillaris and a diagnosis of AMD exists.

Example 4

Expression of mRNAs for Complement Pathway-Associated Proteins by RPE and Coroidal Cells in the Human Eye In order to determine whether the complement components detected in drusen and Bruch's membrane are synthesized remotely (i.e., the liver) or are produced locally by specific ocular cells, total RNA was isolated from the neural retina, the RPE-choroid complex, isolated RPE cells, and liver from human donors. RNA was reverse-transcribed and the resultant cDNA was used as a template for PCR. Genomic DNA isolated from human lymphocytes was used to control for the effects of DNA contamination. Specific complement mediators evaluated are indicated on Table 3. Notably, C3 and C5 are synthesized by the RPE (see also Mullins et al., FASEB J. 2000) as are APP, clusterin, and Factor H. A number of other complement components that are not synthesized by the RPE, such as C9 and MASP-1, are synthesized by adjacent choroidal and/or retinal cells and could therefore contribute to complement activation in Bruch's membrane.

These gene expression data indicate a role for locally produced complement components in the activation of complement in Bruch's membrane and, possibly, in the etiology of early AMD. Some differences in the apparent expression levels of APP2, C3, and C9 were noted in one donor with AMD, but these data were not verified in a larger sample set. Instead, quantitative gene expression studies were initiated to examine differences in expression levels between donors with and without AMD (see Table 4 and Example 4 below).

TABLE 3

Complement Pathway Constituents (RT-PCR)

|         | Ret. | R/Ch | RPE | Gen. DNA | Liver |
|---------|------|------|-----|----------|-------|
| MBL-1   | +    | +    | +   | −        | −     |
| MBL-2 (2) | −  | −    | −   | −        | +     |
| MBPC (1) | −   | −    | −   | −        | +     |
| CRP-1   | −    | −    | −   | −        | +     |
| APP1    | −    | +    | +   | −        | −     |
| APP2    | −    | +    | +   | −        | small |
| MASP1   | −    | +    | −?  | −        | +     |
| C3      | +    | +    | +   | −        | +     |
| C5      | +    | +    | +   | −        | +     |
| C9      | +    | +    | −   | −        | +     |
| HCR1    | +    | +    | −   | −        | +     |
| HCR2    | +/−  | +/−  | +   | +/−      | +     |
| Factor H | +   | +    | +   | −        | +     |
| VN      | +    | +    | −   | −        | +     |
| Clusterin | +  | +    | +   | −        |       |
| CD44    | +    | +    |     | −        |       |
| CD63    | +    | +    | +   | −        | +     |
| CD68    | ?    | +    |     | −        |       |

Example 5

Analyses of Complement Pathway-Associated Component Gene Expression by the RPE and Choroid Using Gene Array Analyses In addition to the patterns of gene expression identified by RT-PCR analyses (above), data derived from gene array analyses have yielded novel information concerning the expression and abundance of specific participants in the complement pathway(s) by the RPE and/or choroid (Table 4). Most significantly, these data confirm that a majority of molecules involved in complement activation and inhibition are expressed locally by RPE and choroid cells. They also provide insight into specific pathways that may be active in the etiology of AMD.

In these studies, mRNA was isolated from 4 mm diameter punches of the equatorial RPE/choroid complex from 78 human donor eyes between the ages of 2 weeks and 101 years. Thirty-one (31) of these donors over the age of 50 had a clinical diagnosis of AMD. The mRNA expression levels of several specific components associated with the complement pathway were compared between this group of 31 AMD donors to those of thirty three (33) age-matched donors without AMD (see Table 4). The local expression of C1q, C1r, C1s, C2 (low abundance), C3, C4, C5, C6 (low abundance), C7, C8 and C9 by RPE and/or choroidal cells has been confirmed and quantified as a function of AMD disease state (Table 4). Moreover, the expression levels of mRNAs for numerous mediators of complement pathways, including mannose binding lectin, factor H, clusterin, vitronectin, and immunoglobulin chain precursors, have been determined and quantified as a function of AMD disease state (Table 4). In addition, these analyses have revealed the expression of numerous additional complement pathway-associated molecules by RPE and/or choroidal cells (Table 4). A number of these molecules are significantly upregulated (e.g. Ig J chain, Ig λ chain) or downregulated (e.g. complement 6, clusterin) in individuals with AMD, as compared to controls. Ongoing studies are being directed toward verification of these data.

TABLE 4

Complement Pathway Constituents (Gene Expression Array Analyses)

| mRNA | Abundance | Control x100 AMD |
|------|-----------|------------------|
| Human Ig J Chain | + | 28% |
| Human Ig λ Chain | ++ | 34% |
| Human IgG Fc Fragment | + | 35% |
| HSP 70 | + | 41% |
| Complement C2 | +/− | 48% |
| CRP | +/− to + | 61% |
| C4 Binding Protein | + | 61% |
| Alpha-2-Macroglobulin | + | 66% |
| Complement C1q | +/++ | 69% |
| Stress Induced Phosphoprotein 1 | + | 70% |
| Heat Shock Protein 75 | + | 72% |
| Complement C3a Receptor 1 | + | 73% |
| Complement C8 Alpha Chain | + | 75% |
| Complement C3 | ++ | 78% |
| Mannose Binding Lectin | + | 80% |
| Ficolin 2 | ++ | 82% |
| Complement C7 | + | 83% |
| Vitronectin | ++ | 87% |
| IgG Fc Binding Protein | ++ | 88% |
| Ig Heavy Chain C Regional a1 | ++ | 88% |
| Complement C9 | + | 90% |
| CD59 | ++ | 90% |
| Factor X | ++ | 92% |
| MBL Serine Protease-2 | + | 92% |
| Complement Component Recep 2 | +/− | 93% |
| Complement 8 Gamma Chain | ++ | 94% |
| Complement C1s | ++ | 95% |
| Ficolin 3 | + | 96% |
| Complement C5 | + | 99% |
| Complement 4a | + | 100% |
| Ficolin-1 | + | 101% |
| Factor H | ++ | 104% |
| Complement C1q Binding Protein | + | 107% |
| Complement C1r | + | 107% |
| Ig Kappa Variable 1D-8 | ++ | 133% |
| Clusterin | ++ | 142% |
| Complement C6 | +/− | 185% |

Abundance (relative signal):
1-1000 (+/−);
1000-50,000 (+);
>50,000 = (++)

Example 6

Characterization of Complement Activation Pathway(s)

Because C5b-9 complexes, if they are present in sufficient quantities at the RPE-choroid interface, are likely cause serious damage to RPE and choroidal cells, we have conducted studies to characterize the mechanism(s) of complement activation in individuals with AMD. At least three pathways of complement activation have been described. These include the classical pathway that is activated via immunoglobulin and C1q, the alternative pathway that is activated at cell surfaces, and the lectin pathway in which the acute phase reactant mannose-binding protein (MBP) activates complement activation along the alternative and/or classical pathways.

Based upon the known molecular relationships in each of these activation pathways, one would predict that, if complement activation occurs along the classical pathway, detectable levels of the immunoglobulins IgG and IgM, as well as C1q, should be present in drusen and Bruch's membrane. On the other hand, if activation occurs along the alternative pathway, Factors H, I, D, and B would be detectable, and if the lectin pathway of activation is involved, mannose-binding protein would be expected to be present.

C1q—an indicator of the classical pathway—is not a major drusen constituent, although it is detected in some drusen. Similarly, other proteins involved in the classical pathway of complement activation are detected only in the choroid, and not in Bruch's membrane and/or drusen. Collectively, these data suggest that the classical pathway may not be the primary pathway involved in the activation of the complement cascade. However, immunoglobulin has been identified within drusen using both biochemical and immunohistochemical approaches (Tables 2 and 4). Thus, immunoglobulin in the form of immune complexes can trigger the classical pathway.

Data collected to date reveal that nearly all of the above major activators of the alternative pathway are present in the drusen and/or the RPE. Six proteins—C3, Factor B, Factor D, Factor H, Factor I and properdin—perform the function of initiation, recognition, and amplification of the alternative pathway, which results in the formation of the activator-bound C3/C5 convertase. The recognition of the alternative pathway activator involves C3b bound to the cell membrane. Factor H—a fluid phase regulator of the alternative pathway of complement that functions to prevent amplification of complement activation by accelerating the decay of C3 and C5 convertases and by acting as a cofactor for factor I-mediated cleavage of surface bound C3b—is a major component of all drusen phenotypes. Further activation of the C3 convertase and cleavage of C3 into smaller molecules results the generation of C3b that propagates an amplification loop. An additional cleavage product from this reaction, the C3d molecule, is also found to be present in all drusen phenotypes.

Mannose binding protein, which is believed to be a potent initiator of the lectin pathway, is also present in all drusen phenotypes, indicating that the lectin pathway can also be operative at the RPE-choroid interface.

The data collected thus far indicate that activation of the complement cascade at the level of the RPE-choroid interface occurs via the alternative and/or lectin pathways, although some activation via the classical pathway can not be ruled out completely at this point. Whatever the exact mechanism of activation, these data provide further evidence that local complement activation occurs at the RPE-choroid interface where it may induce significant tissue damage and pathology.

Example 7

Biochemical Assessment of Plasma Membrane-Associated C5b-9 in RPE and Choroid Cells in Human Donor Eyes Biochemical studies were conducted in order to determine whether C5b-9 complexes are inserted into plasma membranes of RPE and/or choroidal cells in the vicinity of Bruch's membrane. Isolated RPE cells and the RPE/choroid layers from five donors of various ages (two with AMD) were used in these experiments. The samples were homogenized, and plasma membranes were collected using a sucrose gradient ultracentrifugation procedure. Proteins derived from these membrane preparations, as well as the cytosolic supernatant fractions, were tested for the presence of C5b-9 complex by means of ELISA and Western blotting analyses with anti-complement antibodies. Indirect ELISA as well as capture ELISA was performed using a commercial C5b-9 detection kit (Quidel, San Diego).

Figure 3:
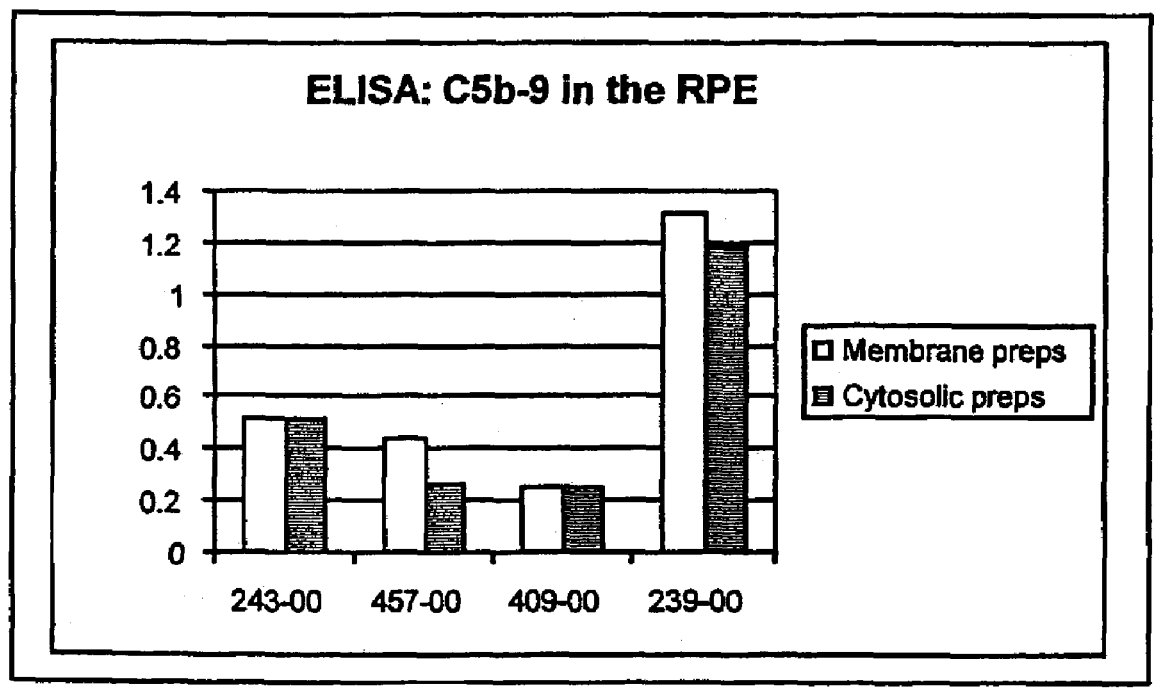
FIG. 3 shows capture ELISA measurements of C5b-9 levels in cytosolic and membrane fractions of isolated human RPE cells from four human donor eyes.
Figure 4:
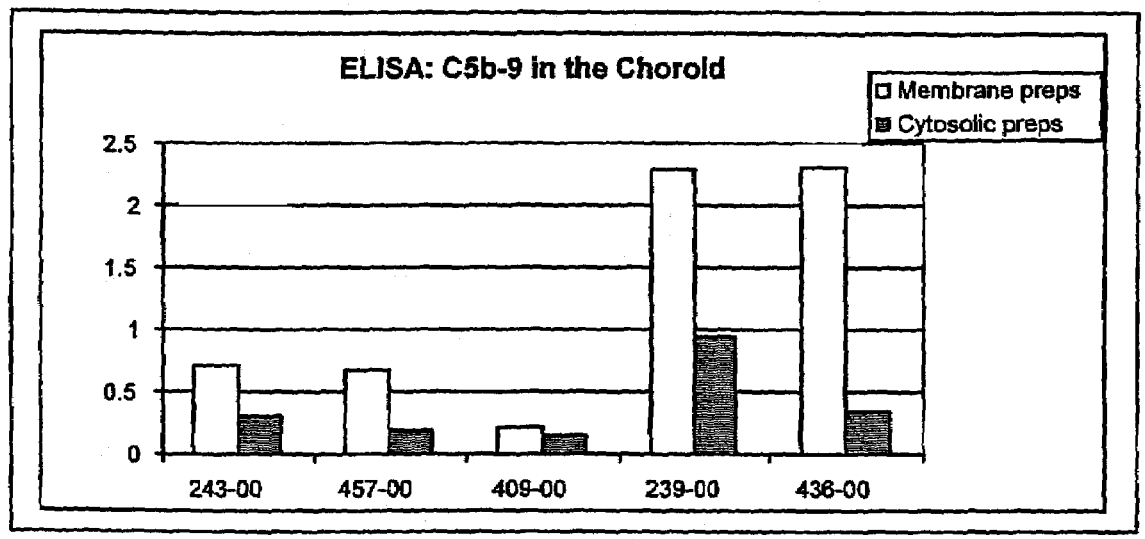
FIG. 4 shows capture ELISA measurements of C5b-9 levels in cytosolic and membrane fractions of human chorioids from 5 donors. The membrane-associated fractions consistently exhibit the highest levels of C5b-9 in these preparations, indicating that a significant proportion of complexes are inserted into plasma membranes of resident and/or transient choroidal cells.
Figure 5:
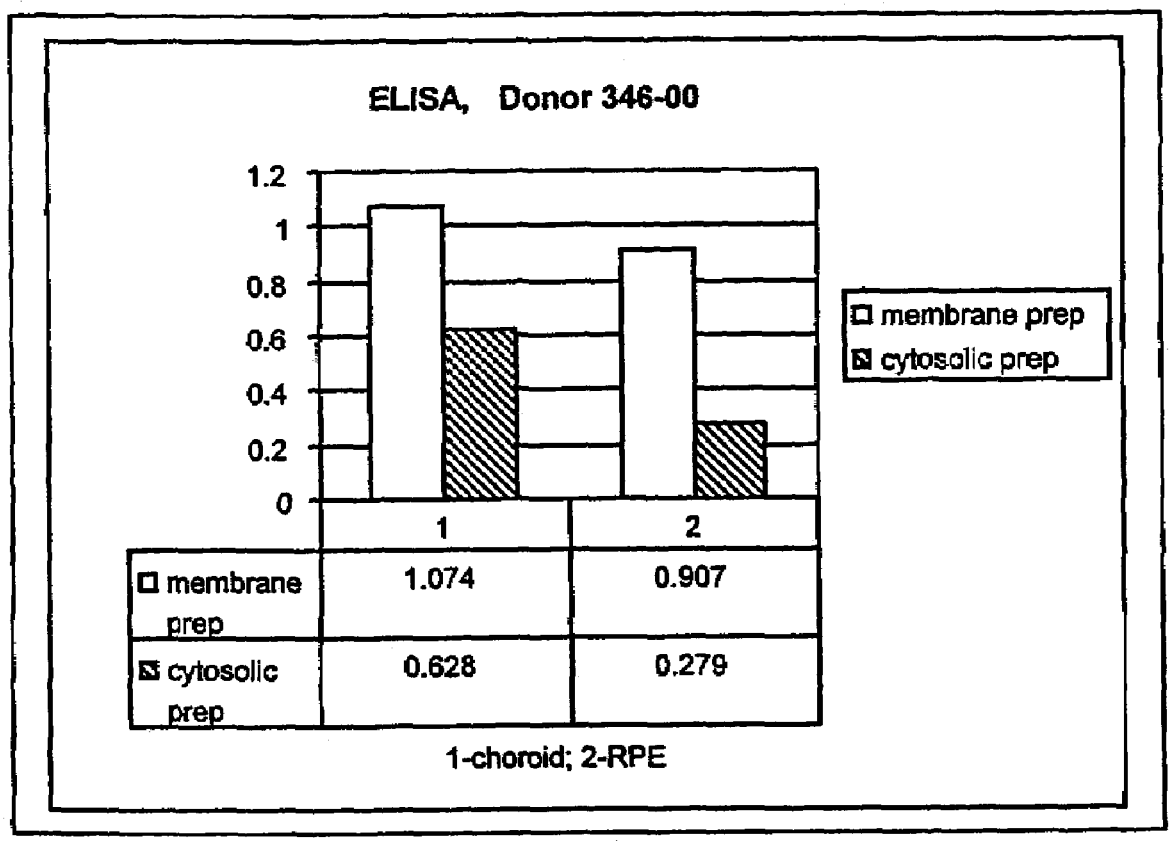
FIG. 5 provides confirmation of capture ELISA results using standard ELISA methodology. Tissues from the following 5 donors (2 of them with AMD) were employed in these experiments.

The results of these analyses demonstrate that the C5b-9 MAC complexes are present, and predominant, in the plasma membranes isolated from the RPE and choroid samples from older donors with and without AMD (FIGS. 3, 4, and 5). In contrast, cells from a ten year old donor (409-00) possess almost undetectable C5b-9 levels in both membrane and cytosolic preparations. The highest levels of C5b-9 is detected in cells from a donor with neovascular AMD (239-00), which supports the hypothesis that complement activation and MAC formation in AMD may be associated with the process of choroidal neovascularization. These differences in C5b-9 levels and distribution between these donors were confirmed immunohistochemical. Intense positive labeling of drusen and Bruch's membrane, as well as some labeling of the choriocapillaris, was observed in the neovascular AMD donor. In contrast, the tissue of the young donor was sporadically, and weakly, positive in some regions of the choroid near Bruch's membrane. In addition, the presence of proteins that are part of the C5b-9 complex was confirmed by Western blot analyses. Positive labeling with antibodies directed against C6 and C9 in RPE membranes and membranes derived from the RPE-choroid complex indicates that membrane insertion of complement complexes does take place in these tissues, and that this insertion may be injurious to the RPE and/or choroid Example 8

Characterization of Drusen Associated with Glomerulonephritis

Many subjects with membranoproliferative glomerulonephritis type II (MPGN-II) are characterized by the presence of deposits within Bruch's membrane that resemble drusen. Glomerulonephritis-associated drusen appear at a younger age, however, than do drusen in individuals with AMD. The structure and composition of drusen in eyes obtained from human donors with two distinct glomerulopathies, both of which involve complement deposition in the glomerulus were examined. Eyes obtained from two human donors diagnosed with membranous and post-streptococcal glomerulonephritis, respectively, were analyzed histochemically, immunohistochemically, and ultrastructurally. These characteristics were compared to those derived from individuals with AMD.

Subretinal pigment epithelial (RPE) deposits in both types of glomerulonephritis are numerous and indistinguishable, both structurally and compositionally, from drusen in donors with AMD. Glomerulonephritis-associated drusen exhibit sudanophilia, bind filipin, and react with antibodies directed against vitronectin, complement C5 and C5b-9 complexes, TIMP-3, and amyloid P component. Drusen from the membranous GN donor, but not the post-streptococcal GN donor, react with peanut agglutinin and antibodies directed against MHC class II antigens and IgG. The ultrastructural characteristics of these deposits were also identical with those of AMD-associated drusen.

These data show that composition and structure of ocular drusen-associated with membranous and post-streptococcal/segmental glomerulonephritis are generally similar to drusen in individuals with AMD. These data support other data which indicate that chronic complement pathway activation is an important contributory factor in drusen biogenesis and Bruch's membrane pathogenesis. It appears that defective complement activation alone may be sufficient to induce the formation of drusen in Bruch's membrane.

Example 9

Autoantibodies in the Sera of Donors with AMD and/or Drusen

It has been observed that serum autoantibodies are present in some AMD subjects. The aim of this study is to determine whether subjects with AMD and ocular drusen have increased levels of specific autoantibodies against complement component when compared to controls without such ocular disorder. The identification of autoantibodies or mediators of complement system provides a diagnostic means for the identification of AMD or other macular degeneration-related disorders.

In order to address the role of autoantibodies in drusen biogenesis and AMD, a series of experiments were performed using enriched drusen preparations in order to identify anti-drusen/Bruch's membrane/RPE autoantibodies that might be present in the sera of donors with AMD and/or drusen.

Protein extracts from an enriched drusen preparation (DR+) obtained by debridement of Bruch's membrane with a #69 Beaver blade and from a control (DR−) preparation were prepared using PBS with proteinase inhibitor cocktail and mild detergent. Proteins were separated by molecular weight using 10-20% gradient mini SDS gels (Amresco) and transferred to PVDF membranes for Western blot analysis. PVDF strips with human retinal proteins from 50 normal human retinas were also used for detection of any anti-retinal autoantibodies in the donor sera.

Sera from the same eight donors described above were screened. Serum from one AMD donor (#90-98) positively labeled a band in the RPE (both DR+ and DR−) and RPE/choroid preparations of approximately 35 kDa A second band of approximately 60 kDa was labeled weakly only in the DR+protein extract. Sera from an AAA donor (#189-97) reacted with a protein(s) of approximately 53 kDa. This band labeled in all three protein extracts. There was one band of approximately 64 kDa that this serum sample labeled only in the DR+ sample.

The presence of serum anti-drusen/RPE autoantibodies in donors with AMD and/or drusen further indicates a possible role for shared immune-mediated processes in these conditions.

Example 10

Analyses of Autoantibodies in the Sera of Living AMD Subjects

In order to determine whether the sera of AMD subjects possesses autoantibodies or alterations in the abundance and/or mobility of serum proteins, plasma was collected from 20 subjects with clinically-diagnosed AMD and from 20 unaffected subjects to serve as controls.

For some experiments, sera were separated by SDS-PAGE and proteins were visualized with either silver stain or Coomassie blue, or (for preparative purposes) proteins were transferred to PVDF membranes for amino acid sequencing. Abnormalities of serum proteins were detected in a subset of AMD donors. These differences included the presence of "additional" bands in the sera of some AMD subjects (molecular weights of ~25, 29, 30 and 80 kDa) that were not present in control donors. Amino acid sequencing of these molecules revealed N-terminal sequences consistent with haptoglobin (25 kDa) and immunoglobulin kappa (29 kDa), lambda (30 kDa), and gamma (80 kDa) chains.

In a second set of experiments, sera from AMD and control donors was screened for the presence of auto-antibodies against RPE and choroid proteins. As an extension of experiments in which weak-moderate immunoreactivity of drusen in tissue sections was previously observed, purified vitronectin was electrophoretically separated and blotted onto PDVF. Because vitronectin had previously been identified as a drusen associated molecule (as detailed in Example 1), the sera from AMD subjects was then evaluated for the presence of anti-vitronectin immunoreactivity. Strong labeling of both the 65 kDa and 75 kDa vitronectin species was identified in these sera, indicating that AMD sera contain autoantibodies directed against at least some drusen-associated molecules and/or Bruch's membrane constituents.

As an additional approach toward the identification of AMD autoantibodies and their targets in ocular tissues, RPE-choroidal proteins from one donor with large numbers of drusen and a nine month old donor were separated electrophoretically according to molecular weight and transferred to nitrocellulose. Proteins were then immunolabeled with either sera from 3 AMD donors or polyclonal antiserum directed against vitronectin. The AMD sera reacted with bands of roughly 65, 150 and 200 kDa only in the sample from the donor with numerous drusen. These results indicate that age and/or the presence of drusen leads to an increase in AMD autoantigen.

Example 11

Autoantibodies Directed Against RPE, Retina, and Fetal Eye Proteins in a Patient with Malattia Leventinese Proteins extracted from the neural retinal, isolated RPE cells, and an entire fetal human eye (96 day) were separated by two-dimensional gel electrophoresis followed by either (a) transfer of the separated proteins to PVDF membranes or (b) silver staining of the 2D gel with a modified solution that is compatible with Matrix Assisted Laser Desorption Ionization (MALDI) mass spectrometry analyses.

Blots were probed with human serum derived from a patient with the early onset macular dystrophy Malattia leventinese, followed by detection of immobilized primary antibodies with alkaline phosphatase-conjugated antibodies directed against human immunoglobulins, and positively labeled spots were matched with the corresponding spots on the silver-stained gels. Silver-stained protein spots corresponding with autoantigens on the Western blots were excised and digested in a solution containing endoproteinase Lys-c/Trypsin, and the resultant peptides were analyzed by matrix assisted-laser desorption ionization mass spectrometry, a technique that permits the identification of a protein based upon the molecular weights of its peptides (Wheeler et al., Electrophoresis, 17(3):580-7 1996). MALDI-MS can be used as a complement to internal amino acid sequencing. In J. Walker (Ed.), The Protein Protocols Handbook (pp. 541-555, Totowa: Humana Press). This technique resulted in the identification of a number of autoantigens within these tissues:

Seven proteins that have been identified from the fetal eye tissue are:
  (i) #1 and #2—MW=27 KD and 25 KD—beta crystallin A4 (Slingsby et al., Exp Eye Res, 51:21-6, 1990);

(ii) #3—MW=25 KD—beta crystallin A2 and trace of beta crystallin A4 (Slingsby et al., supra);
(iii) #4—MW=26 KD—beta crystallin A3 (Slingsby et al., supra);
(iv) #5—MW=18 KD—beta crystallin S (Quax-Jeuken et al., EMBO J, 4(10):2597-602, 1985);
(v) #6—MW=26 KD—beta crystallin A4; and
(vi) #7—MW=80 KD—78 KD glucose-regulated protein Kiang et al., Chin J Physiol, 40:213-9, 1997)

Six proteins were identified from the retinal protein extract:
(i) #1. MW=60 KD-calreticulin (Kovacs et al., Biochemistry, 37(51):17865-74, 1998
(ii) #2. MW=33 KD—possibly complement component 1 (a.k.a glycoprotein GC1QBP, hyaluronan-binding protein; Lynch et al., FEBS Lett, 418(1-2):111-4, 1997)
(iii) #3. MW=29 KD—14-3-3 protein epsilon (Yamanaka et al., Proc Natl Acad Sci USA, 94:6462-7, 1997)
(iv) #4. MW=85 KD—serotransferrin (Campbell et al., J Biol Chem, 252:5996-6001, 1977)
(v) #5. MW=80 KD—albumin
(vi) #6. MW=75 KD—keratin (Hintner et al., 3 Invest Dermatol, 93:656-61, 1989)

Two proteins were identified from the RPE protein extract:
(i) #1. MW=120 KD—pyruvate carboxylase; and
(ii) #2. MW=88 KD—hypothetical protein DKFZp762H157.1 (also called villin 2; Burgess et al., J. Immunol., 1992, 149: 1847-1852, and U.S. Pat. No. 5,773,573).

Example 12

Autoantibodies Directed Against RPE, Choroidal and Retinal Proteins in a Patient with AMD In a separate set of experiments, the serum from donor #189-97 (diagnosed with both AMD and AAA) was employed to probe protein extracts from human choroid (donor 325-00, 77 CF), RPE (donor 318-00, 67 CM) and retina (donor 294-00, 84 CF, AMD) on blots following two-dimensional gel electrophoresis, as described above. Several positively-labeled spots, corresponding to putative autoantigens, were identified. The characteristics of these protein spots were as follows:

Choroidal extract proteins:
(i) three spots were identified with an approximate MW of 86 KD, PI between 5 and 6;
(ii) four spots were identified with an approximate MW of 60 KD, PI between 7 and 8;
(iii) five spots were identified with an approximate MW of 45 KD, PI between 6 and 7;
(iv) 6 spots were identified with an approximate MW between 30 and 43 KD, PI between 4.5 and 6;
(v) 2 spots were identified with an approximate MW of 33 and 35 kD, PI an approximate 7.5;
(vi) 1 spot was identified with MW of 29 KD, PI between 5 and 5.5; and
(vii) 1 spot was identified with an approximate MW of 25 KD, PI approximately 7.5.

RPE extract proteins:
(i) three spots were identified with an approximate MW of 86 KD, PI between 5 and 6;
(ii) three confluent spots were identified with an approximate MW of 95-100K, PI 6.5-7;
(iii) two spots were identified with an approximate MW of 94 KD, PI between 5 and 6;
(iv) one spot was identified with an approximate MW of 60 KD, PI~4.5;
(v) 2 spots were identified with an approximate MW of 33 and 35 kD, PI~7.5; and
(vi) 5 spots were identified with an approximate MW between 35 and 43 KD, PI between 6 and 7;

Retinal extract proteins:
(i) thee confluent spots were identified with an approximate MW of 95-100K, PI 6.5-7;
(ii) 2 spots were identified with an approximate MW of 33 and 35 kD, PI~7.5;
(iii) one spot was identified with an approximate MW of 30-33KD, PI~7;
(iv) several confluent spots were identified with an approximate MW of 60 KD, PI 4-5;
(v) one spot was identified with an approximate MW of 28-30 KD, PI 4.5-5; and
(vi) several spots were identified between 28 and 65 KD with PI from 4 and 7.5.

Example 13

Additional Serological Tests for Markers in Drusen Biogenesis and AMD

Visual acuity measurements, stereo macula photos, and peripheral photos can be taken at the beginning of the study and every six months thereafter. Blood and sera canbe drawn when subjects enter the study and every 6-12 months thereafter. DNA canbe prepared from a portion of each blood sample for future genetic studies. The presence of serum autoantibodies and immune complexes canbe determined using standard protocols. In addition, sera canbe reacted with tissue sections derived from donors with and without AMD, followed by a secondary antibody that has been adsorbed against human immunoglobulins. Western blots of retina/RPE/choroid from AMD and non-AMD donors canalso be incubated with serum samples to identify specific bands against which autoantibodies react.

The presence of antibodies directed against the following proteins (many observed in other age-related conditions and/or MPGN) canalso be determined: type IV collagen, glomerular basement membrane, neutrophils, cytoplasm (c-ANCA, p-ANCA), C3 convertase (C3 nephritic factor), alpha-1 anti-trypsin levels (decreased in MPGN), epsilon 4 allele, apolipoprotein E, GFAP, ANA, serum senescent cell antigen, S-100, type 2 plasminogen activator, alpha-1-antichymotrypsin, SP40,40, endothelial cell, parietal cell, mitochondria, Jo-1, islet cell, inner ear antigen, epidermolysis Bullosa Acquista, endomysial IgA, cancer antigen 15-3, phospholipid, neuronal nucleus, cardiolipin, and ganglioside.

In addition to autoantibodies against complement components, sera from the subject canbe reacted with tissue sections derived from donors with and without AMD, followed by a secondary antibody that has been adsorbed against human immunoglobulins. Western blots of retina/RPE/choroid from AMD and non-AMD donors canalso be incubated with serum samples to identify specific bands against which autoantibodies react.

Further, other than autoantibodies, levels of the following proteins, additional indicators of autoantibody responses, chronic inflammation and/or acute phase responses, canbe assayed by a clinical diagnostic laboratory. These can include Bence Jones protein, serum amyloid A, M components, CRP, mannose binding protein, serum amyloid A, C3a, C5a, other complement proteins, coagulation proteins, fibrinogen, vitronectin, CD25, interleukin 1, interleukin 6, and apolipoprotein E. Serum protein electrophoresis, lymphocyte transformation, sedimentation rate, and spontaneous, whole blood, white cell count canalso be measured. Other proteins that provide additional indication of autoantibody responses, chronic inflammation and/or acute phase responses, canalso be assayed.

What is claimed is:

1. A method for diagnosing the development of age related macular degeneration (AMD) in a subject,
    comprising detecting in a plasma, serum, or whole blood sample from the subject a level of at least one complement pathway protein that is indicative of complement activation and is significantly higher than baseline levels in a control population of subjects without AMD, wherein a level of at least one complement pathway protein that is indicative of complement activation and is significantly higher than baselines levels in the control population indicates that the subject has or is developing AMD, wherein said complement pathway protein is selected from the group consisting of C3, C3a, and C5b-9 terminal complex.

2. The method of claim 1 wherein the complement pathway protein is the C5b-9 terminal complex.

3. The method of claim 1 wherein the complement pathway protein is C3a.

4. The method of claim 1 wherein the complement pathway protein is C3.

5. The method of claim 1, wherein the subject is free of complement related diseases other than AMD.

6. The method of claim 1 wherein the subject does not have clinical symptoms of AMD.

* * * * *